(12) United States Patent
Pol

(10) Patent No.: US 10,881,823 B2
(45) Date of Patent: *Jan. 5, 2021

(54) MEDICAL TUBES FOR SELECTIVE MECHANICAL VENTILATION OF THE LUNGS

(71) Applicant: Guillermo L. Pol, Coral Gables, FL (US)

(72) Inventor: Guillermo L. Pol, Coral Gables, FL (US)

(*) Notice: Subject to any disclaimer, the term of this patent is extended or adjusted under 35 U.S.C. 154(b) by 515 days.

This patent is subject to a terminal disclaimer.

(21) Appl. No.: 15/726,450

(22) Filed: Oct. 6, 2017

(65) Prior Publication Data

US 2018/0093058 A1    Apr. 5, 2018

Related U.S. Application Data

(63) Continuation of application No. 14/082,664, filed on Nov. 18, 2013, now Pat. No. 9,789,271, which is a
(Continued)

(51) Int. Cl.
*A61M 16/04* (2006.01)
*A61B 1/00* (2006.01)
(Continued)

(52) U.S. Cl.
CPC ....... *A61M 16/0434* (2013.01); *A61B 1/0008* (2013.01); *A61B 1/00045* (2013.01);
(Continued)

(58) Field of Classification Search
CPC .............. A61B 1/00045; A61B 1/0008; A61B 1/00082; A61B 1/015; A61B 1/018;
(Continued)

(56) References Cited

U.S. PATENT DOCUMENTS 2,919,697 A    1/1960  Kim
3,071,137 A    1/1963  Niebel et al.
(Continued)

FOREIGN PATENT DOCUMENTS

EP    1 438 980    10/2004
WO    WO 2005/084739    9/2005
(Continued)

OTHER PUBLICATIONS

Watson, "Lung Isolation for Surgery: State of the Art," *Anesthesiology News*, 35(8), pp. 75-89 (Aug. 2009).
(Continued)

*Primary Examiner* — Annette Dixon
(74) *Attorney, Agent, or Firm* — Greenberg Traurig, LLP; David J. Dykeman; Roman Fayerberg

(57) ABSTRACT

A single lumen endobronchial tube for selective mechanical ventilation of the lungs can include a medical tube having a single lumen with an opening at the proximal end of the tube being adapted for connection to an external mechanical ventilation device, and an opening at the distal end being adapted for delivery of a medical gas; a wall extending throughout the tube's entire length having an internal wall surface, an external wall surface and a thickness therebetween, a portion of the wall having an aperture and a shaft adapted to house a mechanism for sealing the aperture; a distal bronchial cuff and at least a first proximal tracheal cuff positioned along the external wall surface and adapted to expand radially outward.

7 Claims, 15 Drawing Sheets

Related U.S. Application Data continuation of application No. 13/021,040, filed on Feb. 4, 2011, now Pat. No. 8,584,678.

(60) Provisional application No. 61/301,435, filed on Feb. 4, 2010.

(51) Int. Cl.
*A61B 1/015* (2006.01)
*A61B 1/018* (2006.01)
*A61B 1/267* (2006.01)
*A61M 16/20* (2006.01)

(52) U.S. Cl.
CPC .......... *A61B 1/00082* (2013.01); *A61B 1/015* (2013.01); *A61B 1/018* (2013.01); *A61B 1/2676* (2013.01); *A61M 16/04* (2013.01); *A61M 16/0404* (2014.02); *A61M 16/0445* (2014.02); *A61M 16/0459* (2014.02); *A61M 16/0486* (2014.02); *A61M 16/20* (2013.01); *A61M 16/201* (2014.02); *A61M 16/202* (2014.02); *A61M 16/0438* (2014.02); *A61M 16/0475* (2014.02); *A61M 2205/502* (2013.01)

(58) Field of Classification Search
CPC . A61B 1/2676; A61M 16/04; A61M 16/0404; A61M 16/0427; A61M 16/0429; A61M 16/0434; A61M 16/0438; A61M 16/0445; A61M 16/0459; A61M 16/0475; A61M 16/0479; A61M 16/0486; A61M 16/20; A61M 16/201; A61M 16/202; A61M 2205/502; A61M 25/04; A61M 25/1011
See application file for complete search history.

(56) References Cited

U.S. PATENT DOCUMENTS

| | | | |
|---|---|---|---|
| 3,331,371 A | 7/1967 | Rocchi et al. | |
| 3,392,722 A | 7/1968 | Jorgensen | |
| 3,592,184 A | 7/1971 | Watkins et al. | |
| 3,964,488 A | 6/1976 | Ring et al. | |
| 4,014,317 A | 3/1977 | Bruno | |
| 4,137,906 A | 2/1979 | Akiyama et al. | |
| 4,140,119 A | 2/1979 | Pollack | |
| 4,166,468 A | 9/1979 | Haynie | |
| 4,186,745 A | 2/1980 | Lewis et al. | |
| 4,233,984 A | 11/1980 | Walling | |
| 4,248,221 A | 2/1981 | Winnard | |
| 4,285,341 A | 8/1981 | Pollack | |
| 4,301,797 A | 11/1981 | Pollack | |
| 4,453,545 A | 6/1984 | Inoue | |
| 4,593,689 A | 6/1986 | White | |
| 4,723,946 A | 2/1988 | Kay | |
| 4,734,094 A | 3/1988 | Jacob et al. | |
| 4,787,882 A | 11/1988 | Claren | |
| 4,850,982 A | 7/1989 | Erlich et al. | |
| 4,968,306 A | 11/1990 | Huss et al. | |
| 5,004,454 A | 4/1991 | Beyar et al. | |
| 5,030,199 A | 7/1991 | Barwick et al. | |
| 5,120,316 A | 6/1992 | Morales et al. | |
| 5,234,409 A | 8/1993 | Goldberg et al. | |
| 5,315,992 A * | 5/1994 | Dalton | A61M 16/04 128/207.15 |
| 5,360,403 A | 11/1994 | Mische | |
| 5,368,579 A | 11/1994 | Sandridge | |
| 5,395,353 A | 3/1995 | Scribner | |
| 5,588,424 A | 12/1996 | Insler et al. | |
| 5,660,175 A | 8/1997 | Dayal | |
| 5,713,877 A | 2/1998 | Davis | |
| 5,771,888 A | 6/1998 | Keim | |
| 5,893,841 A | 4/1999 | Glickman | |
| 5,954,636 A | 9/1999 | Schwartz et al. | |
| 6,550,475 B1 | 4/2003 | Oldfield | |
| 6,609,521 B1 | 8/2003 | Belani et al. | |
| 6,623,421 B1 | 9/2003 | Rodriguez et al. | |
| 6,722,367 B1 | 4/2004 | Blom | |
| 6,786,888 B1 | 9/2004 | Zadno-Azizi et al. | |
| 7,041,080 B2 | 5/2006 | Dion | |
| 7,121,280 B2 * | 10/2006 | Kyle, Jr. | A61M 16/04 128/207.14 |
| 7,204,252 B2 | 4/2007 | Johnson | |
| 7,278,429 B2 | 10/2007 | Johnson | |
| 7,297,105 B2 | 11/2007 | Mackin | |
| 8,584,678 B2 * | 11/2013 | Pol | A61M 16/0445 128/207.15 |
| 9,789,271 B2 | 10/2017 | Pol | |
| 2003/0040671 A1 | 2/2003 | Somogyi et al. | |
| 2004/0144387 A1 | 7/2004 | Amar | |
| 2005/0205097 A1 | 9/2005 | Kyle, Jr. | |
| 2006/0025650 A1 | 2/2006 | Gavriely | |
| 2007/0215162 A1 | 9/2007 | Glassenberg et al. | |
| 2007/0221229 A1 | 9/2007 | Rahaghi et al. | |
| 2008/0021386 A1 | 1/2008 | Clayton | |
| 2008/0072914 A1 | 3/2008 | Hendricksen et al. | |
| 2009/0038621 A1 | 2/2009 | Miller et al. | |

FOREIGN PATENT DOCUMENTS

| | | |
|---|---|---|
| WO | WO 2007/149618 | 12/2007 |
| WO | WO 2009/044192 | 4/2009 |
| WO | WO 2009/070970 | 6/2009 |

OTHER PUBLICATIONS

PCT International Search Report based on PCT/US2011/023689 dated Apr. 19, 2011.
Office action in U.S. Appl. No. 13/021,040 dated Mar. 25, 2013.
European Search Report dated Sep. 29, 2014 for European Patent Application No. 111740394.9.
Non-Final Office Action in U.S. Appl. No. 14/082,664 dated May 5, 2016.
Final Office Action in U.S. Appl. No. 14/082,664 dated Oct. 20, 2016.
Non-Final Office Action in U.S. Appl. No. 14/082,664 dated Mar. 6, 2017.
U.S. Appl. No. 14/082,664, filed Nov. 18, 2013, 2014-0076326, Mar. 20, 2014, U.S. Pat. No. 9,789,271, Oct. 17, 2017, Medical Tubes for Selective Mechanical Ventilation of the Lungs.
U.S. Appl. No. 13/021,040, filed Feb. 4, 2011, 2011-0186053, Aug. 4, 2011, U.S. Pat. No. 8,584,678, Nov. 19, 2013, Medical Tubes for Selective Mechanical Ventilation of the Lungs.

* cited by examiner

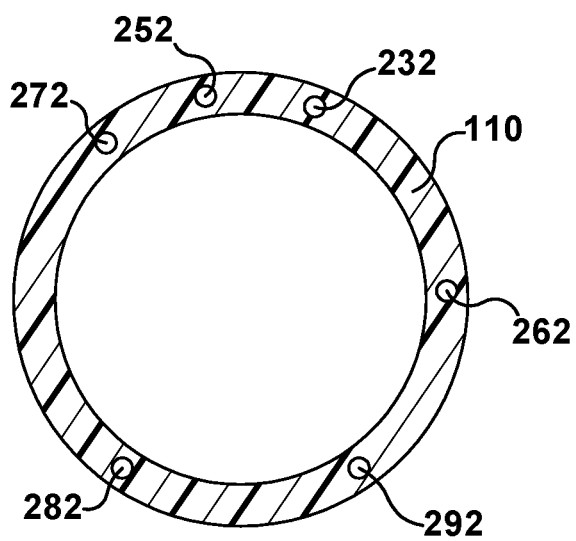
FIG. 3
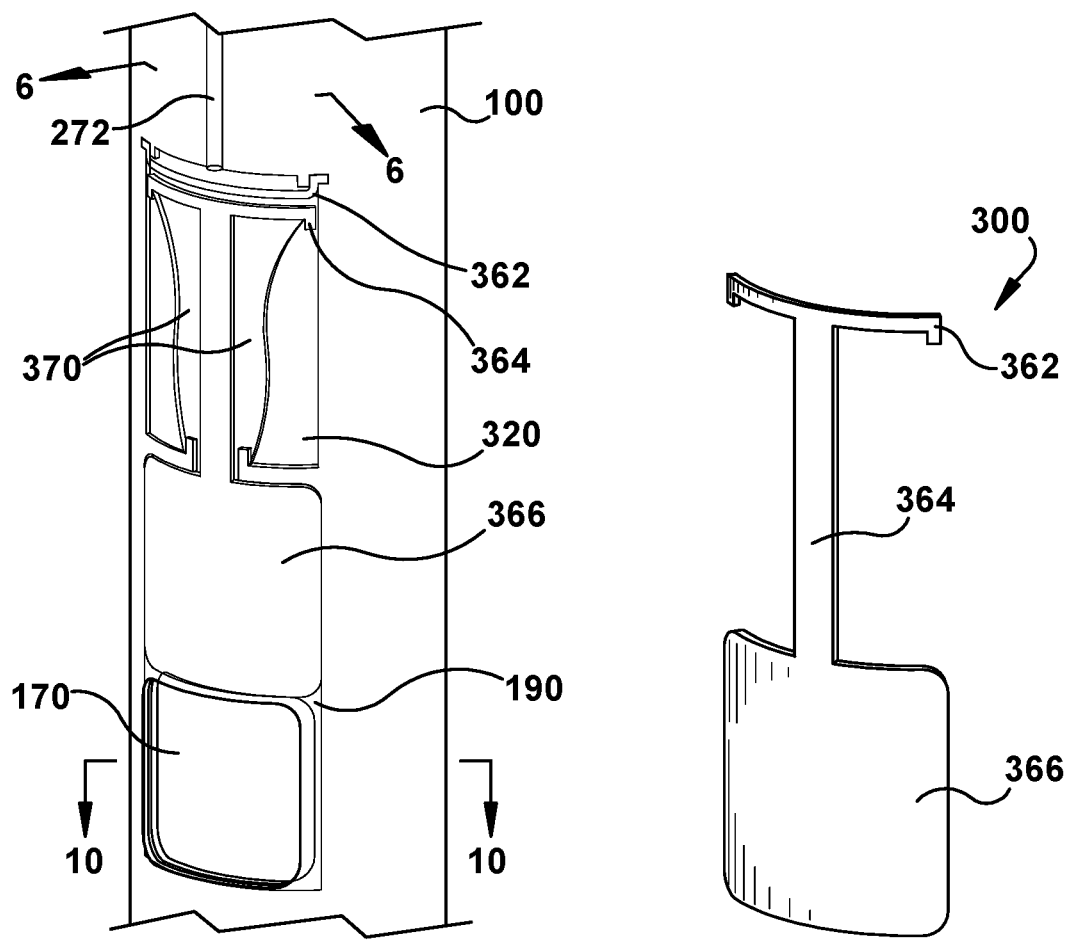
FIG. 4
FIG. 5

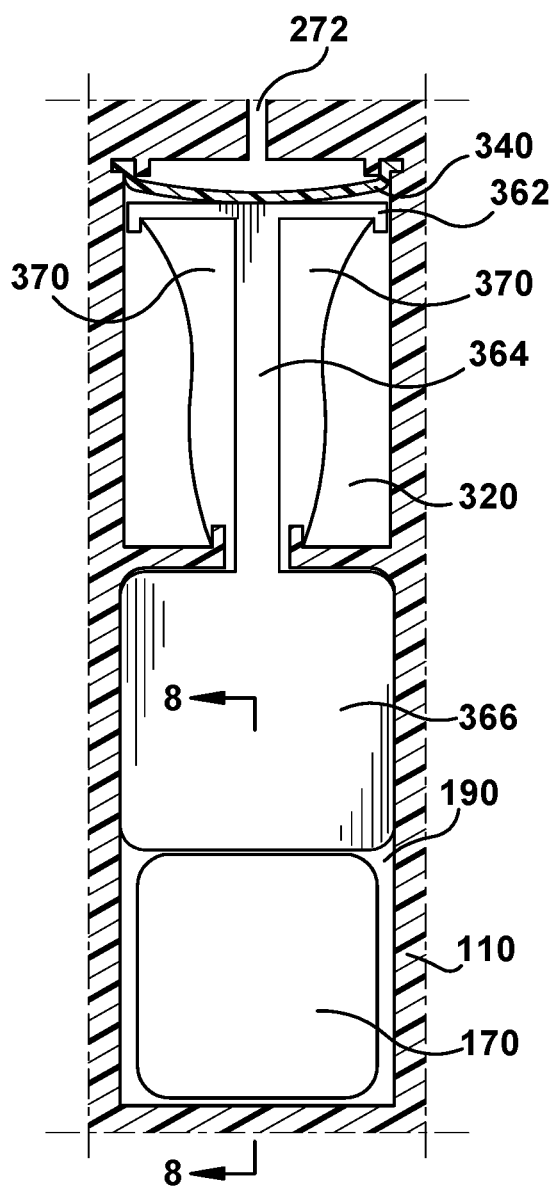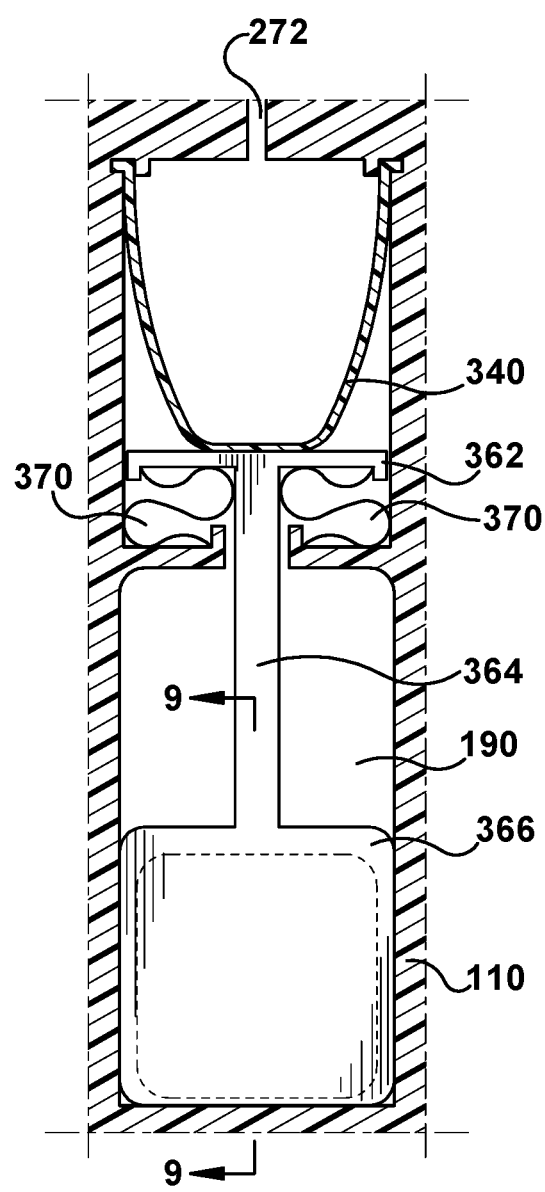

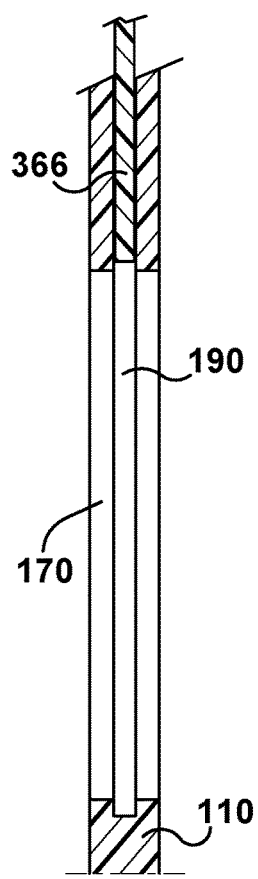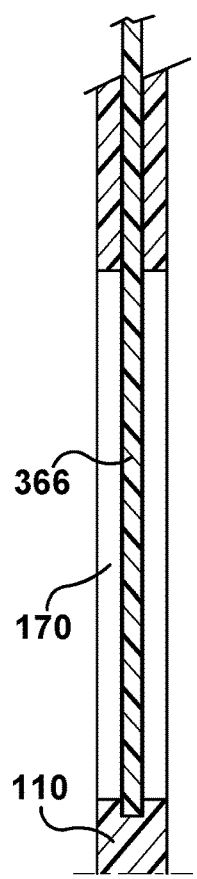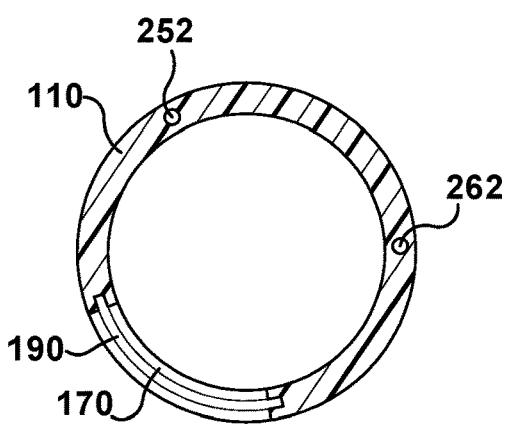
FIG. 8    FIG. 9
FIG. 10
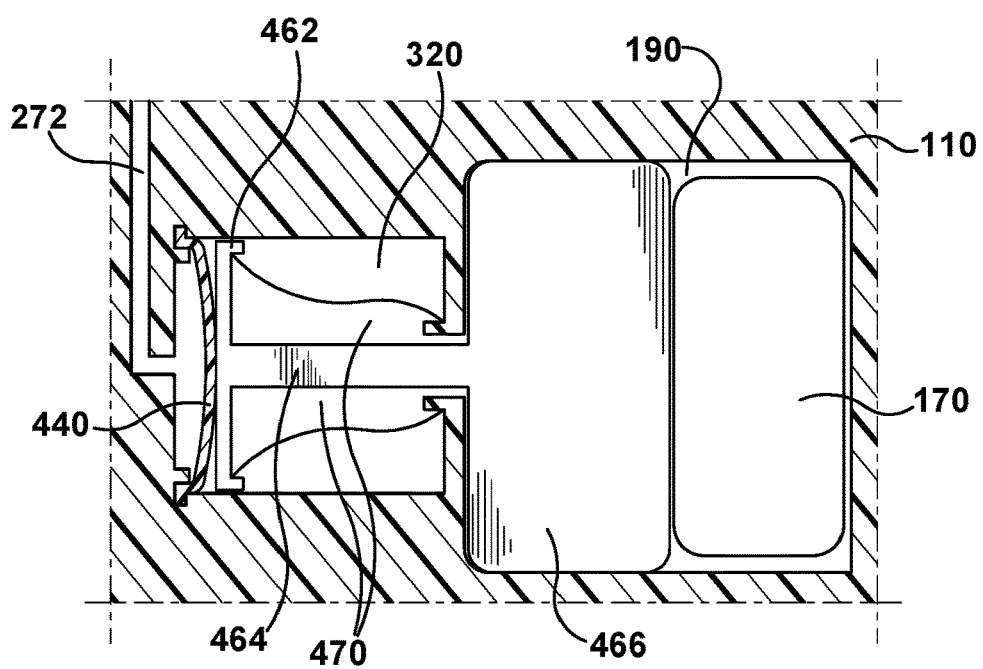
FIG. 11

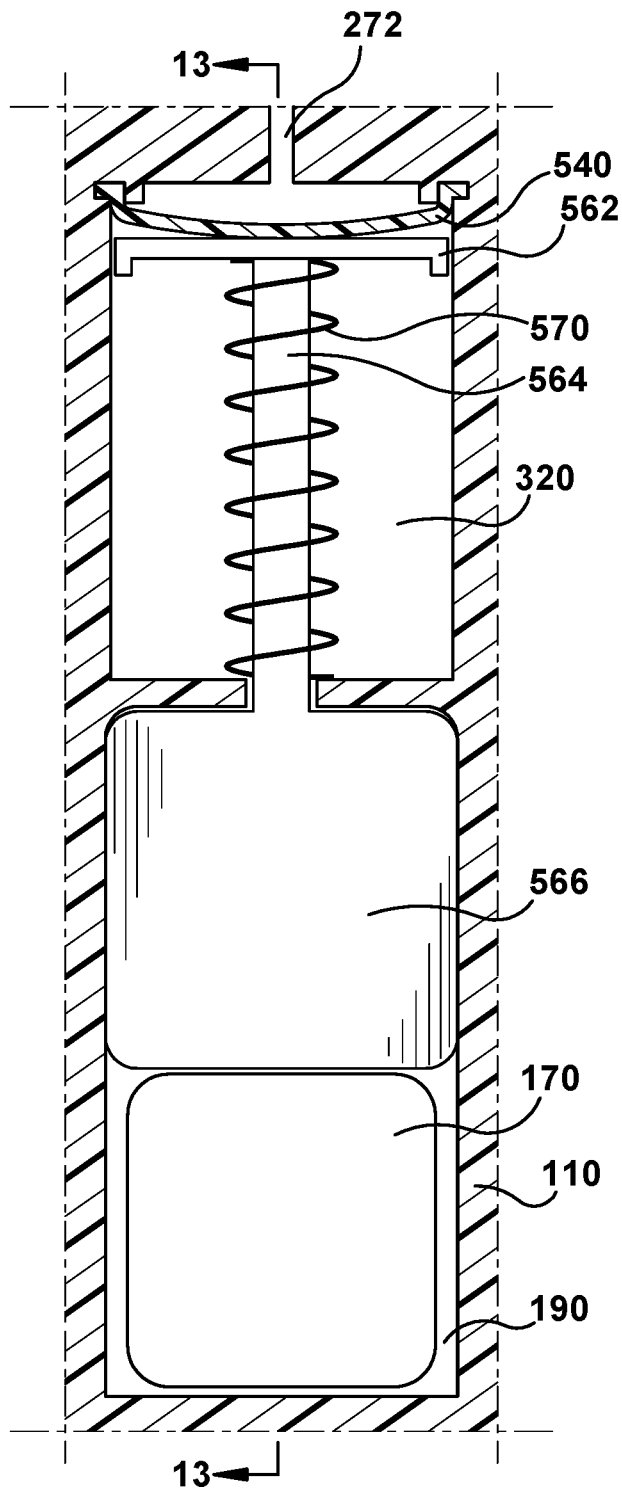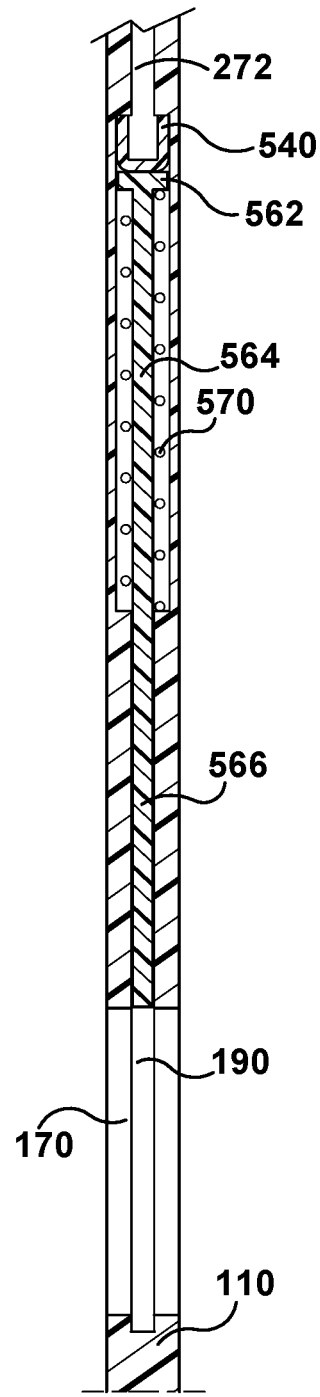
FIG. 12  FIG. 13

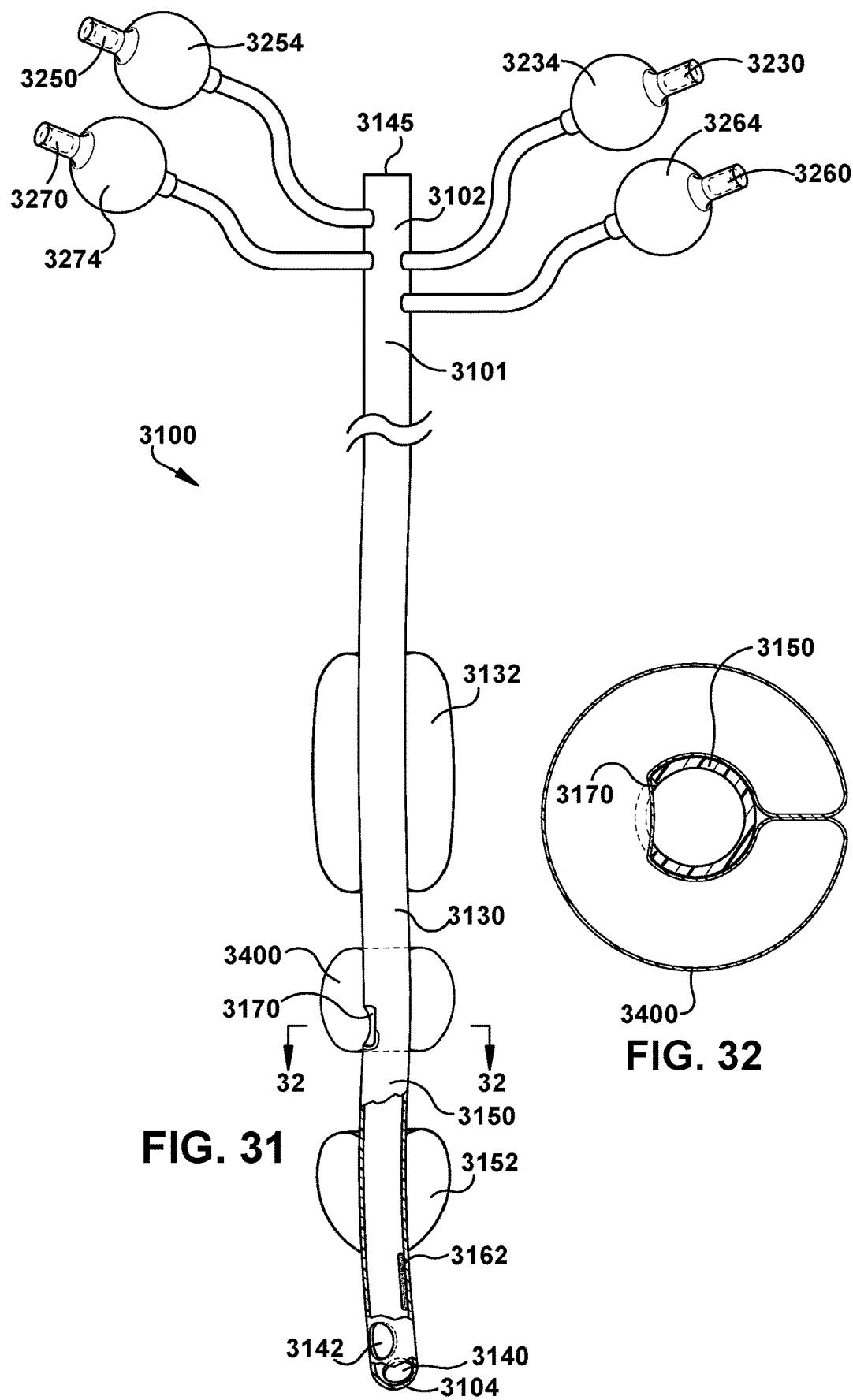

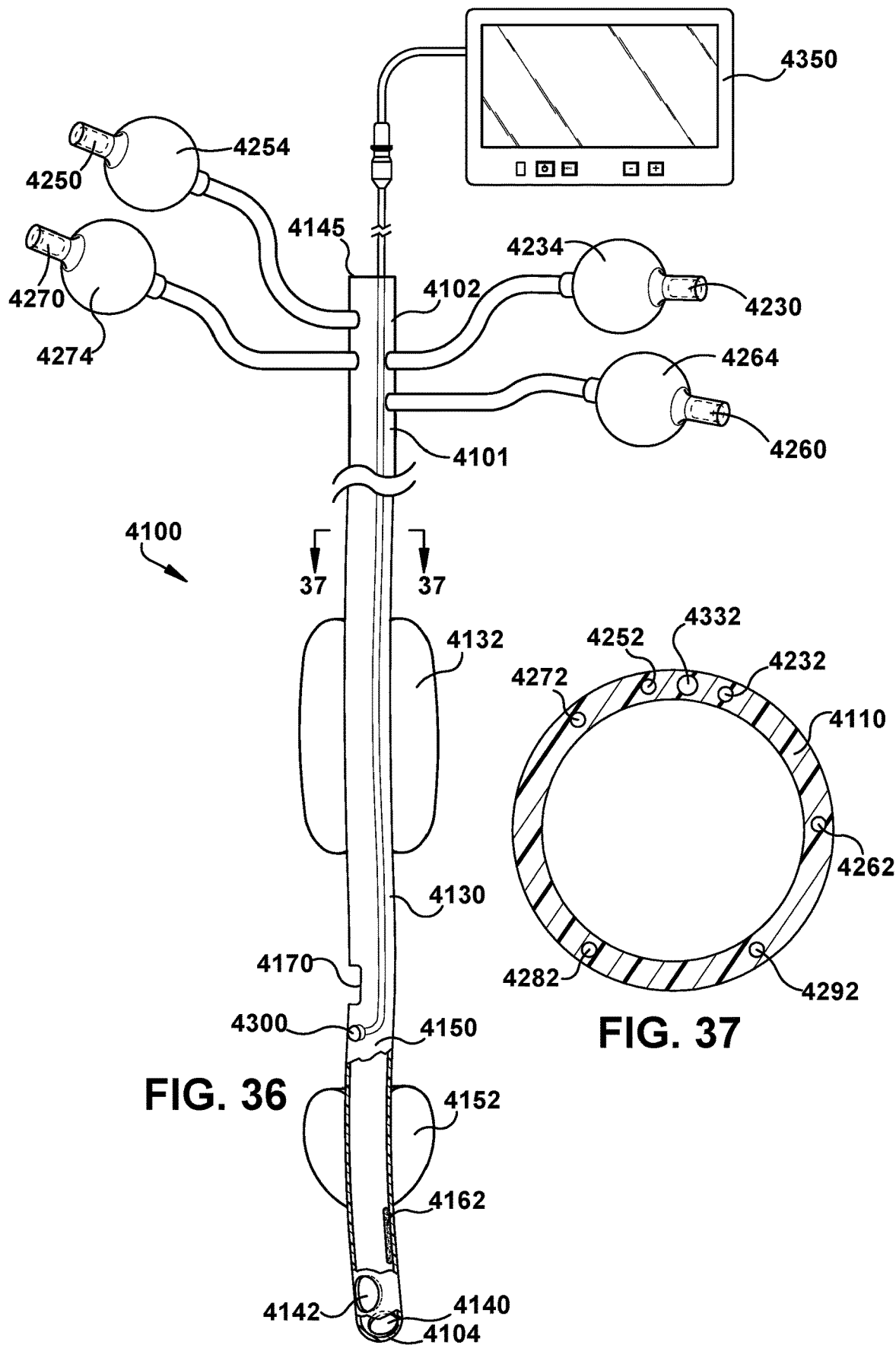

MEDICAL TUBES FOR SELECTIVE MECHANICAL VENTILATION OF THE LUNGS

RELATED APPLICATIONS

This application is a continuation of U.S. application Ser. No. 14/082,664, filed Nov. 18, 2013, now U.S. Pat. No. 9,789,271, which is a continuation of U.S. application Ser. No. 13/021,040, filed on Feb. 4, 2011, now U.S. Pat. No. 8,584,678, and claims the benefit of and priority to U.S. Provisional Application Ser. No. 61/301,435, filed Feb. 4, 2010. These applications are hereby incorporated herein by reference in their entireties for the teachings therein.

FIELD

The embodiments disclosed herein relate to medical tubes for selective mechanical ventilation of the lungs, and more particularly to single lumen endobronchial tubes for selective mechanical ventilation of the left lung or the right lung.

BACKGROUND

The body requires a certain volume of air to be inhaled and exhaled to maintain the correct levels of oxygen and carbon dioxide within the tissues. Tissue damage, which leads eventually to death, occurs if the level of oxygen becomes too low or the amount of carbon dioxide becomes too high. The body is therefore critically dependent on breathing to maintain life. In medicine, mechanical ventilation is a method to mechanically assist or replace spontaneous breathing. A medical ventilator moves breathable air into and out of the lungs, to provide the mechanism of breathing for a patient who is physically unable to breathe, or breathing insufficiently. Ventilators are chiefly used in intensive care medicine and emergency medicine (as stand-alone units) and in anesthesia (as a component of an anesthesia machine).

SUMMARY

Single lumen endobronchial tubes for selective mechanical ventilation of the left lung or the right lung are disclosed herein.

According to aspects illustrated herein, there is provided a single lumen endobronchial tube adapted for isolating a first lung of a patient and ventilating a second lung of the patient that includes a medical tube comprising a tracheal portion and a bronchial portion having a common single lumen and a common tube wall thickness, wherein a proximal end of the tracheal portion includes an opening adapted for connection to an external mechanical ventilation device, and wherein a distal end of the bronchial portion includes an opening adapted for delivery of a medical gas; at least a first tracheal inflatable cuff positioned around an external surface of the tracheal portion and adapted to expand radially outward sealing against the trachea of the patient; a bronchial inflatable cuff positioned around an external surface of the bronchial portion and adapted to expand radially outward against the left main stem bronchi of the patient; an aperture positioned between the tracheal portion and the bronchial portion and adapted to deliver an amount of medical gas to the second lung of the patient; and a mechanism positioned within the wall of the tube, the mechanism adapted to control the amount of medical gas passing through the aperture.

According to aspects illustrated herein, there is provided a single lumen endobronchial tube adapted for isolating a first lung of a patient and ventilating a second lung of the patient that includes a medical tube comprising tracheal portion and a bronchial portion having a common single lumen and a common tube wall thickness, wherein a proximal end of the tracheal portion includes an opening adapted for connection to an external mechanical ventilation device, and wherein a distal end of the bronchial portion includes an opening adapted for delivery of a medical gas; a first tracheal inflatable cuff positioned around an external surface of the tracheal portion and adapted to expand radially outward sealing against the trachea of the patient; a bronchial inflatable cuff positioned around an external surface of the bronchial portion and adapted to expand radially outward against the left main stem bronchi of the patient; a bronchial balloon blocker positioned in the common single lumen of the bronchial portion adapted to expand radially outward sealing the common single lumen; a second tracheal inflatable cuff positioned around an external surface of the tracheal portion and adapted to expand radially outward at a respective distal location relative to the first tracheal inflatable cuff sealing against the trachea of the patient; and an aperture positioned between the first tracheal inflatable cuff and the second inflatable cuff and adapted to deliver an amount of medical gas to the second lung of the patient, wherein the second tracheal cuff is adapted to control the amount of medical gas passing through the aperture.

According to aspects illustrated herein, there is provided a single lumen endobronchial tube adapted for isolating a first lung of a patient and ventilating a second lung of the patient that includes a medical tube comprising a tracheal portion and a bronchial portion having a common single lumen and a common tube wall thickness, wherein a proximal end of the tracheal portion includes an opening adapted for connection to an external mechanical ventilation device, and wherein a distal end of the bronchial portion includes an opening adapted for delivery of a medical gas; at least a first tracheal inflatable cuff positioned around an external surface of the tracheal portion and adapted to expand radially outward sealing against the trachea of the patient; a bronchial inflatable cuff positioned around an external surface of the bronchial portion and adapted to expand radially outward against the left main stem bronchi of the patient; a bronchial balloon blocker positioned in the common single lumen of the bronchial portion adapted to expand radially outward sealing the common single lumen; an aperture positioned between the tracheal portion and the bronchial portion and adapted to deliver an amount of medical gas to the second lung of the patient; and an expandable balloon adapted to control the amount of medical gas passing through the aperture.

According to aspects illustrated herein, there is provided a single lumen endobronchial tube that includes a medical tube comprising a single lumen with an opening at each of opposed distal and proximal ends of the tube, the opening at the proximal end of the tube being adapted for connection to an external mechanical ventilation device, and the opening at the distal end of the tube being adapted for delivery of a medical gas; a wall extending throughout the tube's entire length having an internal wall surface, an external wall surface and a thickness therebetween, a portion of the wall having an aperture and a shaft adapted to house a mechanism for sealing the aperture; a distal bronchial cuff positioned along the external wall surface and adapted to expand radially outward; and at least a first proximal tracheal cuff positioned along the external wall surface and adapted to expand radially outward.

According to aspects illustrated herein, there is provided a single lumen endobronchial tube of the present disclosure that includes a medical tube comprising a single lumen with an opening at each of opposed distal and proximal ends of the tube, the opening at the proximal end of the tube being adapted for connection to an external mechanical ventilation device, and the opening at the distal end of the tube being adapted for delivery of a medical gas; a wall extending throughout the tube's entire length having an internal wall surface, an external wall surface and a thickness therebetween, a portion of the wall having an aperture; a distal bronchial cuff positioned along the external wall surface and adapted to expand radially outward; a first proximal tracheal cuff positioned along the external wall surface and adapted to expand radially outward; and a second proximal tracheal cuff positioned along the external wall surface and adapted to expand radially outward at a respective distal location relative to the aperture.

According to aspects illustrated herein, there is provided a single lumen endobronchial tube of the present disclosure that includes a medical tube comprising a single lumen with an opening at each of opposed distal and proximal ends of the tube, the opening at the proximal end of the tube being adapted for connection to an external mechanical ventilation device, and the opening at the distal end of the tube being adapted for delivery of a medical gas; a wall extending throughout the tube's entire length having an internal wall surface, an external wall surface and a thickness therebetween, a portion of the wall having an aperture; an expandable balloon adapted to control the amount of medical gas passing through the aperture; a distal bronchial cuff positioned along the external wall surface and adapted to expand radially outward; and at least a first proximal tracheal cuff positioned along the external wall surface and adapted to expand radially outward.

According to aspects illustrated herein, there is provided a method for one-lung ventilation of a lung of an air-breathing animal that includes providing a single lumen endobronchial tube, the single lumen endobronchial tube comprising a medical tube having a single lumen with an opening at each of opposed distal and proximal ends of the tube, the opening at the proximal end of the tube being adapted for connection to an external mechanical ventilation device, and the opening at the distal end of the tube being adapted for delivery of a medical gas; a wall extending throughout the tube's entire length having an internal wall surface, an external wall surface and a thickness therebetween, a portion of the wall having an aperture and a shaft adapted to house a mechanism for sealing the aperture; a distal bronchial cuff positioned along the external wall surface and adapted to expand radially outward; at least a first proximal tracheal cuff positioned along the external wall surface and adapted to expand radially outward; and a distal intraluminal balloon blocker at a respective distal location relative to the aperture; positioning the single lumen endobronchial tube in the pulmonary airway of the animal such that the distal bronchial cuff is in the left main stem bronchus, and the first proximal tracheal cuff is in the trachea, wherein a distal end of the medical tube is positioned beyond the carina of the animal; connecting the proximal end of the medical tube to the external mechanical ventilation device; inflating the distal bronchial cuff radially outwardly to seal against the surrounding bronchus of the left lung; inflating the proximal tracheal cuff radially outwardly to seal against the surrounding trachea of the animal; and performing a step selected from one of inflating the distal intraluminal balloon blocker radially outwardly to occlude the lumen of the tube and thereby effectively occlude the left lung, whereby an airway from the ventilation device to the animal's right lung is maintained via the aperture or sealing the aperture by activating the mechanism housed in the shaft of the wall of the tube to block the aperture and thereby effectively occlude the right lung, whereby an airway from the ventilation device to the animal's left lung is maintained via the opening at the distal end of the tube.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 2A shows a distal intraluminal balloon of the single lumen endobronchial tube in an inflated state. FIG. 2B shows a distal intraluminal balloon of the single lumen endobronchial tube in a deflated state.

FIG. 3 shows a cross-sectional plan view taken along line 3-3 of FIG. 1.

FIG. 4 shows a partial perspective view of the single lumen endobronchial tube of FIG. 1 showing an embodiment of a mechanism adapted to control the amount of medical gas passing through an aperture provided through a wall of the tube.

FIG. 5 shows a component of the mechanism of FIG. 4 adapted to control the amount of medical gas passing through the aperture provided through the wall of the tube.

FIG. 6 shows a cutaway side view taken along line 6-6 of FIG. 4 when the mechanism is adapted to allow the passage of medical gas through the aperture provided through the wall of the tube.

FIG. 7 shows a cutaway side view taken along line 6-6 of FIG. 4 when the mechanism is adapted to prevent the passage of medical gas through the aperture provided through the wall of the tube.

FIG. 8 shows a cross-sectional view taken along line 8-8 of FIG. 6.

FIG. 9 shows a cross-sectional view taken along line 9-9 of FIG. 7.

FIG. 10 shows a cross-sectional plan view taken along line 10-10 of FIG. 4.

FIG. 11 shows a cutaway side view of the single lumen endobronchial tube of FIG. 1 showing an embodiment of a mechanism adapted to control the amount of medical gas passing through an aperture provided through a wall of the tube.

FIG. 12 shows a cutaway side view of the single lumen endobronchial tube of FIG. 1 showing an embodiment of a mechanism adapted to control the amount of medical gas passing through an aperture provided through a wall of the tube.

FIG. 13 shows a cross-sectional view taken along line 13-13 of FIG. 12.

As illustrated in FIG. 14, the mechanism is adapted to allow the passage of medical gas through the aperture provided through the wall of the tube. As illustrated in FIG. 15, the mechanism is adapted to prevent the passage of medical gas through the aperture provided through the wall of the tube.

As illustrated in FIG. 16, the mechanism is adapted to allow the passage of medical gas through the aperture provided through the wall of the tube.

As illustrated in FIG. 17, the mechanism is adapted to allow the passage of medical gas through the aperture provided through the wall of the tube. As illustrated in FIG. 18, the mechanism is adapted to prevent the passage of medical gas through the aperture provided through the wall of the tube.

As illustrated in FIG. 21, the mechanism is adapted to allow the passage of medical gas through the aperture provided through the wall of the tube. As illustrated in FIG. 22, the mechanism is adapted to prevent the passage of medical gas through the aperture provided through the wall of the tube.

As illustrated in FIG. 23, the mechanism is adapted to allow the passage of medical gas through the aperture provided through the wall of the tube. As illustrated in FIG. 24, the mechanism is adapted to prevent the passage of medical gas through the aperture provided through the wall of the tube.

As illustrated in FIG. 25, the mechanism is adapted to allow the passage of medical gas through the aperture provided through the wall of the tube. As illustrated in FIG. 26, the mechanism is adapted to prevent the passage of medical gas through the aperture provided through the wall of the tube.

FIG. 31 is a side view of an embodiment of a single lumen endobronchial tube of the present disclosure.

FIG. 32 shows a cross-sectional plan view taken along line 32-32 of FIG. 31.

As illustrated in FIG. 33, the balloon is adapted to allow the passage of medical gas through the aperture provided through the wall of the tube. As illustrated in FIG. 34, the balloon is adapted to prevent the passage of medical gas through the aperture provided through the wall of the tube.

FIG. 36 is a side view of an embodiment of a single lumen endobronchial tube of the present disclosure.

FIG. 37 shows a cross-sectional plan view taken along line 37-37 of FIG. 36.

Figures 1, 2A, 2B:
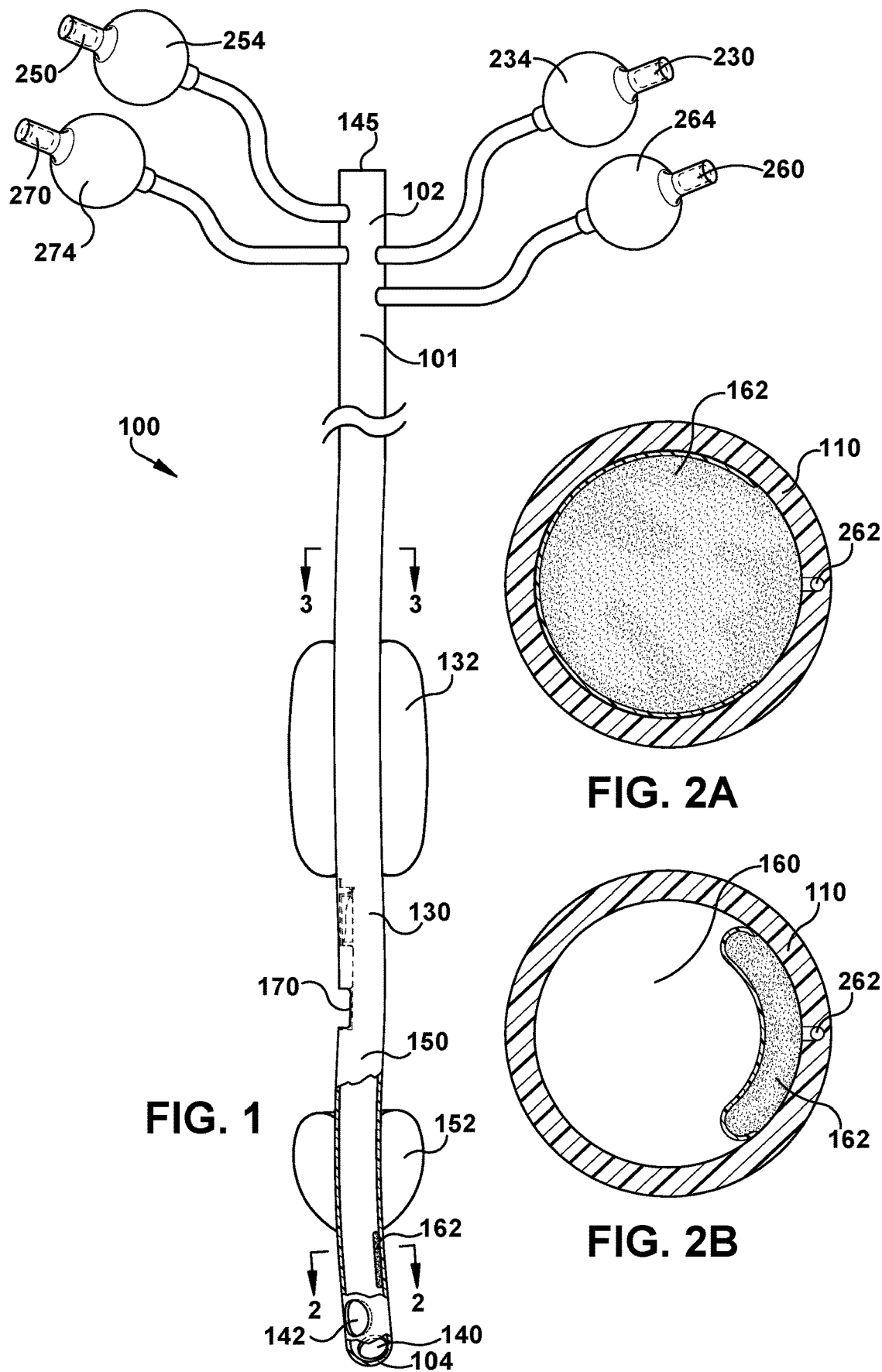
FIG. 1 is a side view of an embodiment of a single lumen endobronchial tube of the present disclosure.
FIG. 2A and FIG. 2B are cross-sectional plan views taken along line 2-2 of FIG. 1.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Mechanical ventilation has become the most commonly used mode of life support in medicine today. Widely used in management of acutely ill surgical and ICU patients, mechanical ventilation can also be used in the chronic support of patients with a wide spectrum of chronic diseases that can cause respiratory failure.

As used herein, the term "anesthesia machine" refers to a machine used by an anesthesiologist to support the administration of anesthesia. The most common type of anesthesia machine, the continuous-flow anesthesia machine, is designed to provide an accurate and continuous supply of medical gases (such as oxygen and nitrous oxide), mixed with an accurate concentration of anesthetic vapor (such as isoflurane), and deliver this to the patient at a safe pressure and flow. Modern machines incorporate a medical ventilator, suction unit, and patient-monitoring devices.

As used herein, the term "positive airway pressure" or "PAP" refers to a method of respiratory ventilation used primarily in the treatment of sleep apnea. PAP ventilation is also commonly used for critically ill patients in hospital with respiratory failure, and in newborn infants (neonates). "Bilevel Positive Airway Pressure" or "BIPAP" refers to a form of temporary respiratory support for patients that have difficulty breathing. Each time the patient breathes, the BIPAP machine assists the patient by applying air pressure to the lungs while the patient is breathing out (exhaling or expiration) in order to hold open the air sacs in the lungs. "Continuous Positive Airway Pressure" or "CPAP" refers to the application of positive pressure to the airways of the spontaneously or mechanically breathing patient throughout the respiratory cycle. A CPAP machine uses continuous air pressure to produce added oxygen or simply to help keep the airways in the lungs open. The air pressure keeps the airways functioning properly and helps the individual breathe additional oxygen more easily. CPAP machines were initially used mainly by patients for the treatment of sleep apnea at home, but now are in widespread use across intensive care units as a form of ventilation.

As used herein, the term "mechanical ventilation" refers to a method to mechanically assist or replace spontaneous breathing.

As used herein, the term "external mechanical ventilation device" refers to a machine to mechanically assist or replace spontaneous breathing. Examples of external mechanical ventilation devices include, but are not limited to, hand-controlled ventilators and mechanical ventilators such as transport ventilators, ICU ventilators, and PAP ventilators (BiPAP machine, CPAP machine).

As used herein, the term "medical gas" includes gases such as compressed air, oxygen, carbon dioxide, helium, nitrogen and nitrous oxide.

As used herein, the term "one-lung ventilation", "OLV", "independent lung ventilation" or "ILV" consists of mechanical ventilation of a selected lung and exposure or intentional airway blocking to the other. OLV is required for a number of thoracic procedures, including, but not limited to, lung surgery, esophageal surgery, aortic surgery, mediastinal surgery, minimally invasive lung surgery, minimally invasive heart surgery, robotic heart surgery and robotic lung surgery. In a conventional OLV procedure, a double-lumen endotracheal tube, an endobronchial blocker, or a single lumen tube may be used. Double-lumen endotracheal tubes and endobronchial blockers function differently. Double-lumen endotracheal tubes isolate ventilation, separating the right and left pulmonary units using two separate endotracheal tubes. An endobronchial blocker blocks ventilation to a pulmonary segment. Endobronchial blockers are typically balloon tipped catheters that are placed in the portion of the pulmonary tree that is to be blocked (usually the right or left main stem bronchus). Ventilation to the pulmonary unit is blocked when the balloon is inflated.

As used herein, the term "positive pressure ventilation" or "PPV" refers to the process of forcing air into the lungs of a patient.

As used herein, the term "pulmonary airway" refers to those parts of the respiratory system through which air flows, conceptually beginning (on inhalation from the external environment) at the nose and mouth, and terminating in the alveoli. From the mouth or nose, inhaled air passes through the pharynx into the trachea, where the air separates into the left and right main bronchi at the carina, situated at the level of the second thoracic vertebra. The main bronchi then branch into large bronchioles, one for each lobe of the lung. Within the lobes, the bronchioles further subdivide some 20 times, ending in clusters of alveoli.

As used herein, the term "tracheal intubation" refers to the placement of a flexible plastic tube into the trachea to protect the patient's airway and provide a means of mechanical ventilation. The most common tracheal intubation is orotracheal intubation where, with the assistance of a laryngoscope, an endotracheal tube is passed through the mouth, larynx, and vocal cords, into the trachea. Another possibility is nasotracheal intubation where a tube is passed through the nose, larynx, vocal cords, and trachea.

Disclosed herein are medical tubes for selective mechanical ventilation of the left lung or the right lung. FIG. 1 in conjunction with FIG. 2A, FIG. 2B and FIG. 3, show an embodiment of a single lumen endobronchial tube 100 of the present disclosure. The single lumen endobronchial tube 100 is a medical tube that includes a proximal end 102, a distal end 104, and a primary flow passage or lumen 160 passing therebetween. The distal end 104 of the tube 100 has a bronchial opening 140. In an embodiment, the bronchial opening 140 is smooth and beveled, thus minimizing risk of tracheal intubation airway trauma. The distal end 104 of the tube 100 can optionally include a Murphy eye 142, which is a distal opening in a wall 110 and through an outer surface 101 of the tube 100 which can allow airflow in the event of the bronchial opening 140 lying against the tracheal wall or being obstructed in other ways. Located at the proximal end 102 of the tube 100 is an opening 145 sufficiently designed to connect with a mechanical ventilation device, including, but not limited to, an anesthesia machine or a PAP machine, with or without the use of an adaptor. The tube 100 includes a tracheal portion 130 and a bronchial portion 150. The tube 100 may be made from a flexible material including, but not limited to, latex, silicone, polyvinyl chloride (PVC), polyurethane (PU), polytetrafluoroethylene or a similar material that has met the American National Standard for Anesthetic Equipment; ANSI Z-79 standard and implant-tested to ensure nontoxicity. In an embodiment, the tube 100 is made from a non-toxic, clear, PVC material. In an embodiment, the tracheal portion 130 is adapted to follow the natural contour of a patient's trachea, and the bronchial portion 150 is adapted to follow the natural contour of a patient's left main stem bronchi. In an embodiment, to facilitate passage of the bronchial portion 150 into the left main stem bronchi, the tube 100 is curved or bent and resembles the shape of a hockey stick. In an embodiment, the angle of the bend is about 45°. The lumen 160 of the tube 100 is sized and dimensioned to allow other instrumentation to pass through the lumen 160 as required. The removal of mucous, the injection of medication, or the insertion of fiberoptic scopes for viewing within the tube 100 are examples of the additional instrumentation capability which is afforded by the tube 100. In an embodiment, the single lumen endobronchial tube 100 may be referred to as a left-sided single lumen endobronchial tube.

A tracheal cuff 132 and a bronchial cuff 152 are spaced longitudinally along an exterior surface of the tracheal portion 130 and the bronchial portion 150, respectively. In an embodiment, the tracheal cuff 132 and the bronchial cuff 152 are thin walled, high volume low pressure (HVLP) balloon-like members sealed from fluid communication with the tube 100 and adapted not to compromise the blood flow in the tracheal or bronchial wall when inflated. The tracheal cuff 132 and the bronchial cuff 152 are shown in an expanded state in FIG. 1. In an embodiment, the balloon-like members are spherical or elliptical in shape, although any desired shape is possible and within the scope and spirit of the present disclosure. In an embodiment, the walls of the tracheal cuff 132 and the bronchial cuff 152 are on the order of about 5 µm to about 500 µm, about 5 µm to about 250 µm, about 5 µm to about 100 µm, about 5 µm to about 50 µm, about 5 µm and about 20 µm, about 5 µm and about 15 µm.

It is also contemplated that the walls may have a thickness of less than about 5 µm. Additionally, although the thickness of the walls may vary, it is desirable that the thickness of the material remain consistent throughout the cuff. A distal intraluminal balloon blocker 162 adapted to inflate and deflate is positioned along an inner surface of the tube 100 and when inflated acts to block flow by blocking ventilation to the left main stem bronchus. In an embodiment, the distal intraluminal balloon blocker 162 is a low volume high pressure member. In an embodiment, the member is spherical or elliptical in shape, although any desired shape is possible and within the scope and spirit of the present disclosure.

The tracheal cuff 132, the bronchial cuff 152, and the distal intraluminal balloon blocker 162 are each remotely and selectively inflatable through pilot tubes 232, 252 and 262, respectively, running longitudinally through the wall 110 of the tube 100 as shown in FIG. 3. The wall 110 has an internal wall surface, an external wall surface and a thickness therebetween. Each pilot tube 232, 252 and 262 emerges from the outer surface 101 of the tube 100 near the proximal end 102 of the tube 100. Attached to a proximal end of each pilot tube 232, 252 and 262 is a non-return valve 230, 250 and 260 which is adapted to receive the nozzle of a syringe (not visible) and a complementary indicator bladder 234, 254 and 264 which enables an anesthesiologist to confirm that each of the tracheal cuff 132, the bronchial cuff 152, and the distal intraluminal balloon blocker 162 has been inflated or deflated. The non-return valves 230, 250 and 260 may be attached to a syringe for injecting a predetermined quantity of air. Various materials may be used to form the tracheal cuff 132, the bronchial cuff 152 and the distal intraluminal balloon blocker 162. These materials include, but are not limited to, polyurethane (PU), low-density polyethylene (LDPE), polyvinyl chloride (PVC), silicone, neoprene, polyisoprene, polyamid (PA) or polyethylene teraphthalate (PETP). Additionally, copolymer admixtures for modifying the characteristics of the material may be used, for example a low density polyethylene and ethylene-vinylacetate copolymer (LDPE-EVA), or blends of the above mentioned materials (e.g. PU with PVC or PU with PA) would be considered suitable for forming the tracheal cuff 132, the bronchial cuff 152 and the distal intraluminal balloon blocker 162.

An aperture 170 is provided through the wall 110 of the tube 100 between the tracheal cuff 132 and the bronchial cuff 152, as best illustrated in FIG. 1. The aperture 170 can be of any shape or size. In an embodiment, the aperture 170 is dimensioned so that a fiberoptic scope can pass through the aperture 170. A shaft adapted to house components of a mechanism, the components of the mechanism sufficiently designed to seal the aperture 170, is created in the wall 110 of the tube 100. Various embodiments of shafts and mechanism components are described in detail below. In the embodiments described in FIGS. 4-13 below, the shaft is made up of two compartments, a chamber and a track housing. In the embodiments described in FIGS. 14-20 below, the shaft is made up of one compartment, a track housing. The components of the mechanism are adapted to control the amount of medical gas passing through the aperture 170. In an embodiment, the components of the mechanism are adapted to completely close and seal the aperture 170 such that the amount of medical gas passing through the aperture 170 from the lumen 160 is 0%. In an embodiment, the components of the mechanism are adapted to partially close the aperture 170 such that the amount of medical gas passing through the aperture 170 from the lumen 160 is greater than 0% but less than 100%. In an embodiment, the components of the mechanism for controlling the flow of medical gas through the aperture 170 are remotely controlled through a pilot tube 272 running longitudinally through the wall 110 of the tube (see FIG. 3). The pilot tube 272 emerges from the outer surface 101 near the proximal end 102 of the tube 100. Attached to a proximal end of the pilot tube 272 is a non-return valve 270 which is adapted to receive the nozzle of a syringe (not visible), and an indicator bladder 274 which enables an anesthesiologist to confirm that the mechanism has moved to close or seal the aperture 170. The non-return valve 270 may be attached to a syringe for injecting a predetermined quantity of air, saline or any other fluid.

In some embodiments, the single lumen endobrochial tube is adapted for use with a PAP machine. In such embodiments, conduits 282 and 292 (see FIG. 3) run longitudinally through the wall 110 of the tube 100 to deliver gas to a patient at positive pressure in order to hold open alveoli that would normally close at the end of expiration. The tube 100 can be manufactured to various sizes and adapted to provide mechanical ventilation to an air-breathing animal in need thereof. In an embodiment, the tube 100 is manufactured for human use and ranges in size from about 1.5 mm to about 11.0 mm in internal diameter (ID). In an embodiment, the tube 100 is manufactured for human use and ranges in size from about 3 mm to about 10 mm in internal diameter (ID). In an embodiment, the tube 100 is manufactured for non-human use and ranges in size from about 1.5 mm to about 40.0 mm in internal diameter (ID). In an embodiment, the tube 100 is manufactured for non-human use and ranges in size from about 6.0 mm to about 40.0 mm in internal diameter (ID).

Various embodiments of shafts and mechanism components adapted to control the amount of medical gas passing through the aperture 170 will now be discussed. The mechanism components disclosed herein are adapted to partially or completely close the aperture 170 such that the amount of medical gas passing through the aperture 170 from the lumen 160 ranges from about 0% to about 100%. In an embodiment, the aperture 170 is fully closed and adapted to provide 100% of the medical gas to ventilate the left lung (i.e., 0% of the medical gas ventilates the right lung). In an embodiment, the aperture 170 is fully open and adapted to provide 100% of the medical gas to ventilate the right lung (i.e., % of the medical gas ventilates the left lung). In an embodiment, the aperture 170 is partially open and adapted to provide about 50% of the medical gas to ventilate the left lung and about 50% of the medical gas to ventilate the right lung. Such an embodiment can be beneficial during the final stage of a medical procedure where a medical practitioner does not have to reposition the tube 100 to ventilate both the left lung and the right lung. A mechanism of the present disclosure is controlled by a user of the tube 100, typically an anesthesiologist, such that selective ventilation of the left lung or the right lung is achievable without the need to move or reposition the tube 100. This is highly beneficial to a patient, since postintubation repositioning of a medical tube can be highly dangerous.

FIG. 4 in conjunction with FIG. 5, FIG. 6 and FIG. 7 show an embodiment of a mechanism adapted to control the amount of medical gas passing through the aperture 170. The components of the mechanism are positioned within the wall 110 of the tube 100 such that the components are adapted to move in a frontal plane parallel to the central longitudinal axis of the tube 100. An inner sealed diaphragm 340 is in fluid communication with the pilot tube 272 and separates a chamber 320 from the pilot tube 272. A piston 300 having a base portion 362 engaging the diaphragm 340, and a rod portion 364 engaging a door portion 366, is powered by leaf springs 370 surrounding the rod portion 364, and is moveable along a longitudinal plane substantially parallel to a central longitudinal axis of the tube 100. By pushing fluid (such as air) through pilot tube 272, the diaphragm 340 is inflated (as illustrated in FIG. 6 and FIG. 7). The base portion 362 and the rod portion 364 of the piston 300 move within the chamber 320 and the door portion 366 moves within a track housing 190. FIG. 8 shows a cross-sectional view taken along line 8-8 of FIG. 6. FIG. 9 shows a cross-sectional view taken along line 9-9 of FIG. 7. FIG. 10 shows a cross-sectional plan view taken along line 10-10 of FIG. 4.

FIG. 11 shows a cutaway side view of an embodiment of a mechanism adapted to control the amount of medical gas passing through the aperture 170. The components of the mechanism are positioned within the wall 110 of the tube 100 such that the components are adapted to move in an axial plane perpendicular to the central longitudinal axis of the tube 100. An inner sealed diaphragm 440 is in fluid communication with the pilot tube 272 and separates the chamber 320 from the pilot tube 272. A piston having a base portion 462 engaging the diaphragm 440, and a rod portion 464 engaging a door portion 466, is powered by fluid (air), and leaf springs 470 surrounding the rod portion 464 bring the piston back when the fluid pressure is off. The piston is moveable along a plane substantially parallel to a central longitudinal axis of the tube 100. By pushing fluid (such as air) through pilot tube 272, the diaphragm 440 is inflated. The base portion 462 and the rod portion 464 of the piston move within the chamber 320 and the door portion 466 moves within the track housing 190.

FIG. 12 shows a cutaway side view of an embodiment of a mechanism adapted to control the amount of medical gas passing through the aperture 170. The components of the mechanism are positioned within the wall 110 of the tube 100 such that the components are adapted to move in a frontal plane parallel to the central longitudinal axis of the tube 100. An inner sealed diaphragm 540 is in fluid communication with the pilot tube 272 and separates a chamber 320 from the pilot tube 272. A piston having a base portion 562 engaging the diaphragm 540, and a rod portion 564 engaging a door portion 566, is powered by fluid (air), and spring 570 surrounding the rod portion 564 bring the piston back when the fluid pressure is off. The piston is moveable along a longitudinal plane substantially parallel to a central longitudinal axis of the tube 100. By pushing fluid (such as air) through pilot tube 272, the diaphragm 540 is inflated. The base portion 562 and the rod portion 564 of the piston move within the chamber 320 and the door portion 566 moves within the track housing 190.

In an embodiment, the sealed diaphragm described in any of FIGS. 4-13 is made of a flexible or stretchable elastomeric material, including, but not limited to, silicone rubber. In an embodiment, the piston described in any of FIGS. 4-13 is fabricated from a non-degradable biocompatible natural or synthetic polymer, a biocompatible flexible metal, or combinations thereof. In an embodiment, the piston is manufactured from a polystyrene material. In an embodiment, the piston is manufactured from a nitinol material. In an embodiment, the piston described in any of FIGS. 4-13 is sufficiently shaped to follow the radius of curvature of the tube 100 (see, for example, FIG. 5). In an embodiment, the sealed diaphragm described in any of FIGS. 4-13, the piston described in any of FIGS. 4-13, and the spring described in any of FIGS. 4-13 may be fabricated from a disposable material and suitable for one-time use. In an embodiment, the sealed diaphragm described in any of FIGS. 4-13, the piston described in any of FIGS. 4-13, and the spring described in any of FIGS. 4-13 may be fabricated from a sterilizable material and suitable for re-use.

Figure 14:
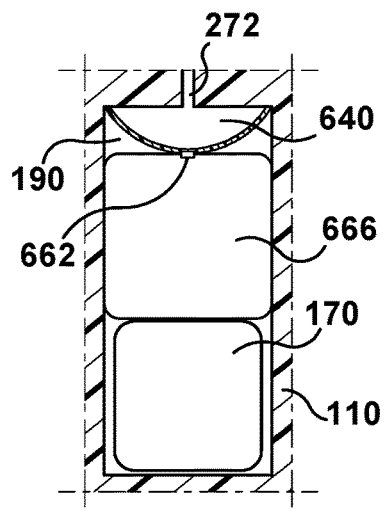
FIG. 14 and FIG. 15 show cutaway side views of the single lumen endobronchial tube of FIG. 1 showing an embodiment of a mechanism adapted to control the amount of medical gas passing through an aperture provided through a wall of the tube.
Figure 15:
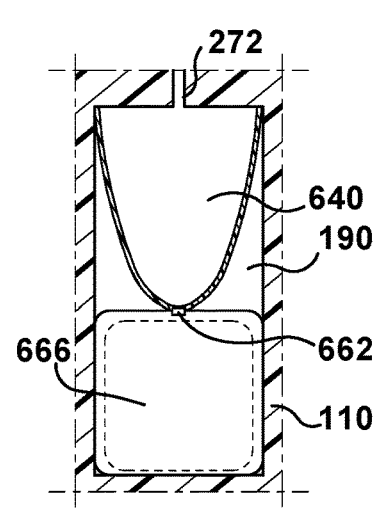
Figure 16:
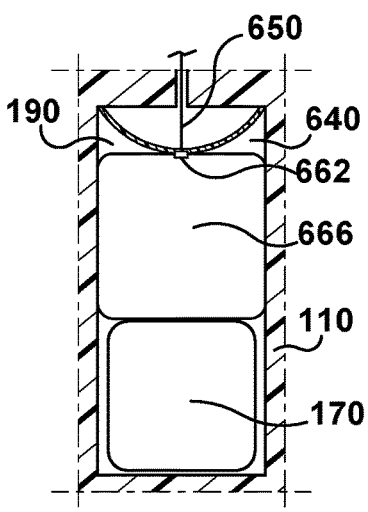
FIG. 16 shows a cutaway side view of the single lumen endobronchial tube of FIG. 1 showing an embodiment of a mechanism adapted to control the amount of medical gas passing through an aperture provided through a wall of the tube.

FIG. 14 in conjunction with FIG. 15 shows cutaway side views of an embodiment of mechanism adapted to control the amount of medical gas passing through the aperture 170. The components of the mechanism are positioned within the wall 110 of the tube 100 such that the components are adapted to move in a frontal plane parallel to the central longitudinal axis of the tube 100. A balloon (or inner sealed diaphragm) 640 is in fluid communication with the pilot tube 272 and engages a door portion 666 moveable within the track housing 190. In an embodiment, the balloon 640 is a low volume high pressure member. The door portion 666 is controlled by pushing fluid (such as air) through pilot tube 272 to inflate the balloon 640 which moves the door portion 666 to cover the aperture 170 (FIG. 15). As illustrated in FIG. 14 and FIG. 15, the door portion 666 is sufficiently shaped to follow the radius of curvature of the tube 100. As described above, the door portion 666 can be fabricated from a non-degradable biocompatible natural or synthetic polymer, a biocompatible flexible metal, or combinations thereof. In an embodiment, the door portion 666 is manufactured from a polystyrene material. In an embodiment, the door portion 666 is manufactured from a nitinol material. In an alternative embodiment, as illustrated in FIG. 16, a wire 650 can be attached to the door portion 666 through the balloon 640 to aid movement of the door portion 666. The wire 650 can be manufactured from a host of materials, including, but not limited to, stainless steel, aluminum, copper, nickel, nitinol, teflon, polypropylene or similar material. Although the embodiments illustrated in FIG. 14 and FIG. 15 show the components adapted to move in a frontal plane parallel to the central longitudinal axis of the tube 100, it should be understood that the components of the mechanism can be positioned within the wall 110 of the tube 100 such that the components are adapted to move in an axial plane perpendicular to the central longitudinal axis of the tube 100, similar to what was illustrated in FIG. 11.

Figure 17:
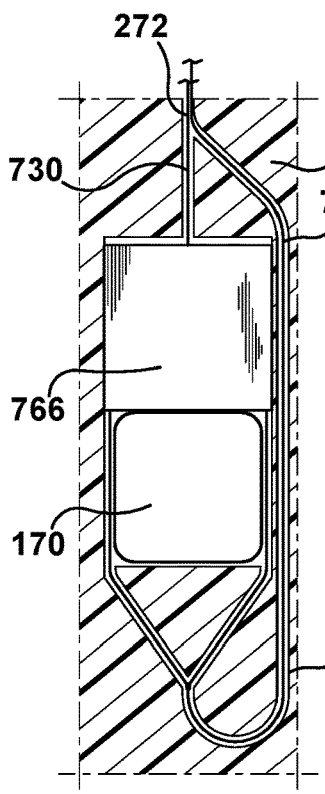
FIG. 17 and FIG. 18 show cutaway side views of the single lumen endobronchial tube of FIG. 1 showing an embodiment of a mechanism adapted to control the amount of medical gas passing through an aperture provided through a wall of the tube.
Figure 18:
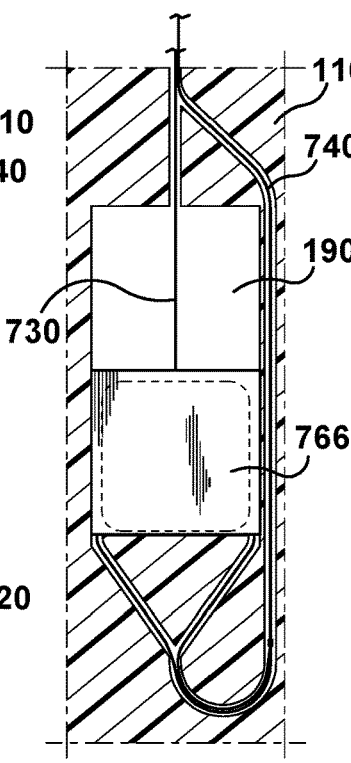

FIG. 17 in conjunction with FIG. 18 shows cutaway side views of an embodiment of mechanism adapted to control the amount of medical gas passing through the aperture 170. The components of the mechanism are positioned within the wall 110 of the tube 100 such that the components are adapted to move in a frontal plane parallel to the central longitudinal axis of the tube 100. A door portion 766 engages a first wire 730 at a proximal end of the door portion 766, the first wire 730 traveling through pilot tube 272 and exiting at the proximal end 102 of the tube 100; and also engages two wires at a distal end of the door portion 766 that combine to form wire 740 traveling through channels generally represented by 720 leading to pilot tube 272 and exiting at the proximal end 102 of the tube 100. The door portion 766 is controlled by a user controlling the wires 730 and 740 at the proximal end 102 of the tube 100. In such an embodiment, the components labeled 270 and 274 in FIG. 1, along with the tube leading into pilot tube 272, are not necessary. The wire 730 moves within the pilot tube 272 and the two wires that combine to form wire 740 move within the channels generally represented by 720. To move the door portion 766 from the resting position in track housing 190 to over the aperture 170, wire 740 is pulled relative to wire 730. To move the door portion 766 so that the door portion 766 no longer covers the aperture 170, wire 730 is pulled relative to wire 740. As illustrated in FIG. 17 and FIG. 18, the door portion 766 is sufficiently shaped to follow the radius of curvature of the tube 100. As described above, the door portion 766 can be fabricated from a non-degradable biocompatible natural or synthetic polymer, a biocompatible flexible metal, or combinations thereof. In an embodiment, the door portion 766 is manufactured from a polystyrene material. In an embodiment, the door portion 766 is manufactured from a nitinol material. Although the embodiments illustrated in FIG. 17 and FIG. 18 show the components adapted to move in a frontal plane parallel to the central longitudinal axis of the tube 100, it should be understood that the components of the mechanism can be positioned within the wall 110 of the tube 100 such that the components are adapted to move in an axial plane perpendicular to the central longitudinal axis of the tube 100, similar to what was illustrated in FIG. 11.

Figure 19:
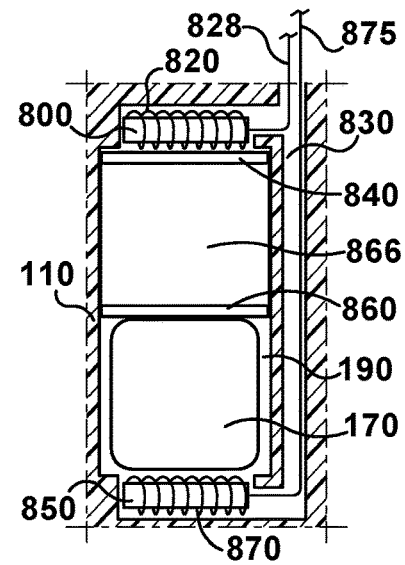
FIG. 19 shows a cutaway side view of the single lumen endobronchial tube of FIG. 1 showing an embodiment of a mechanism adapted to control the amount of medical gas passing through an aperture provided through a wall of the tube.

FIG. 19 shows an embodiment of a mechanism adapted to control the amount of medical gas passing through the aperture 170. The mechanism includes a first electromagnet 800 having a conductor (coiled wire 820) wound around a core, a second electromagnet 850 having a conductor (coiled wire 870) wound around a core, and a door portion 866. As illustrated in FIG. 19, the door portion 866 includes ferrous metal plates 840 and 860 that can either be added to the door portion 866 or built-in to the door portion 866. The ferrous metal plates 840 and 860 can magnetically engage the electromagnets 850 and 800. The electromagnets 850 and 800 can be connected to an external current source (for example an AC or DC current source) via wires 828 and 875 travelling through channels running longitudinally through the wall 110 of the tube 100 to create a magnetic field capable of moving the door portion 866 to either cover the aperture 170 or maintain the aperture 170 open, as illustrated in FIG. 19.

Figure 20:
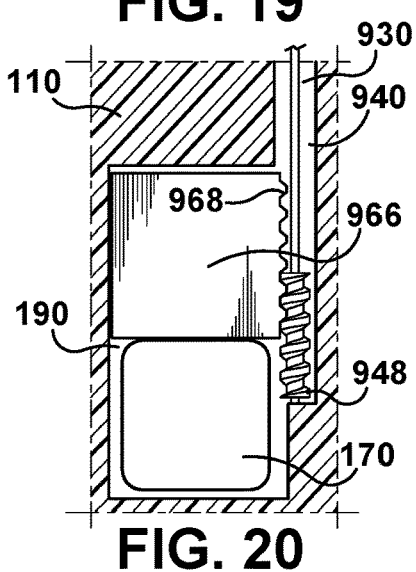
FIG. 20 shows a cutaway side view of the single lumen endobronchial tube of FIG. 1 showing an embodiment of a mechanism adapted to control the amount of medical gas passing through an aperture provided through a wall of the tube.

FIG. 20 shows an embodiment of a mechanism adapted to control the amount of medical gas passing through the aperture 170. The mechanism includes a door portion 966 having teeth 968, the teeth 968 engaging teeth 948 of a rotatable shaft 940. A proximal end (not visible) of the shaft 940 emerges from the proximal end 102 of the tube 100, where a user can rotate the shaft 940 causing the teeth 948 to catch the teeth 968 of the door portion 960, thus moving the door portion 960 as necessary to control the amount of medical gas passing through the aperture 170.

Figure 21:
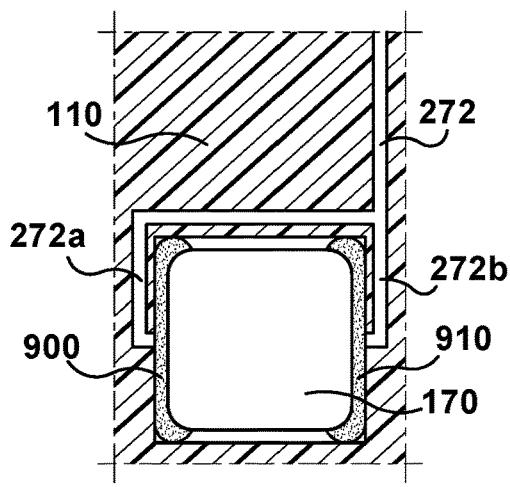
FIG. 21 and FIG. 22 show cutaway side views of the single lumen endobronchial tube of FIG. 1 showing an embodiment of a mechanism adapted to control the amount of medical gas passing through an aperture provided through a wall of the tube.
Figure 22:
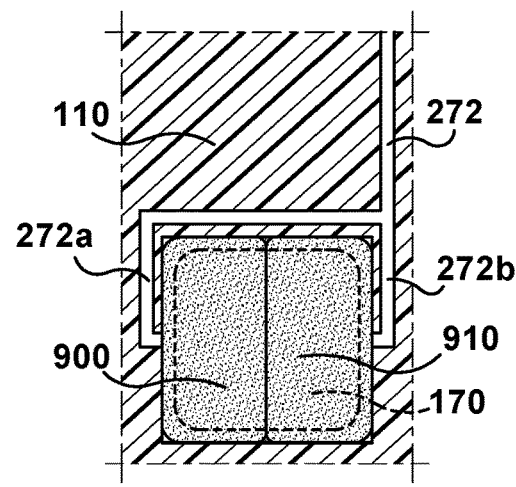

FIG. 21 in conjunction with FIG. 22 shows cutaway side views of a mechanism adapted to control the amount of medical gas passing through the aperture 170. The components of the mechanism are positioned within the wall 110 of the tube 100 such that the components are adapted to move in a frontal plane parallel to the central longitudinal axis of the tube 100 to cover the aperture 170 when required. As illustrated in FIG. 21, the mechanism includes a first expandable balloon 900 and a second expandable balloon 910 both in fluid communication with the pilot tube 272 via tubes 272a and 272b, respectively. By pushing fluid (such as air) through pilot tube 272, and thus 272a and 272b, the first expandable balloon 900 and the second expandable balloon 910 are inflated (as illustrated in FIG. 22). In the embodiment illustrated in FIG. 21 and FIG. 22, when the balloons 900 and 910 are inflated, the balloons 900 and 910 expand from an outer boundary of the aperture 170 towards the middle of the aperture 170 until they meet to substantially cover the aperture 170 to prevent medical gas from escaping. In an embodiment, the first expandable balloon 900 and the second expandable balloon 910 are low volume high pressure members. In an embodiment, the first expandable balloon 900 and the second expandable balloon 910 are high volume low pressure members. Although not illustrated in FIG. 21 and FIG. 22, in an embodiment, pilot tubes 272a and 272b each separately run longitudinally through the wall 110 of the tube so that each of the balloons 900 and 910 can independently be expanded or deflated.

Figure 23:
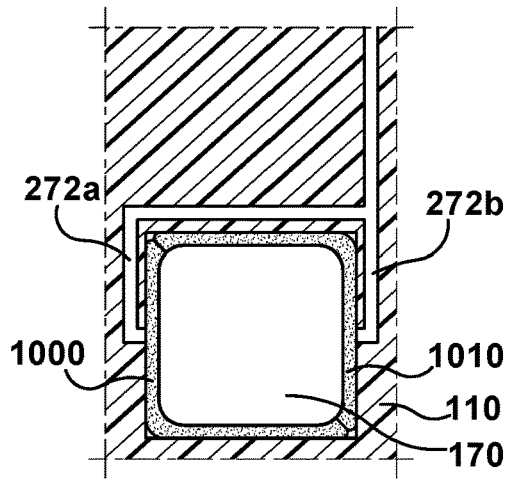
FIG. 23 and FIG. 24 show cutaway side views of the single lumen endobronchial tube of FIG. 1 showing an embodiment of a mechanism adapted to control the amount of medical gas passing through an aperture provided through a wall of the tube.
Figure 24:
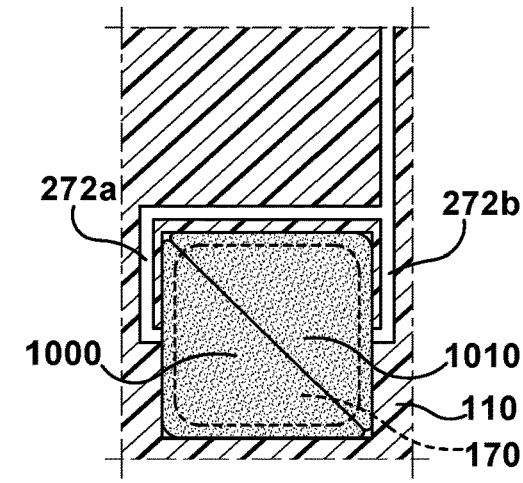

FIG. 23 in conjunction with FIG. 24 shows cutaway side views of a mechanism adapted to control the amount of medical gas passing through the aperture 170. The components of the mechanism are positioned within the wall 110 of the tube 100 such that the components are adapted to move in a frontal plane parallel to the central longitudinal axis of the tube 100 to cover the aperture 170 when required. As illustrated in FIG. 23, the mechanism includes a first expandable balloon 1000 and a second expandable balloon 1010 both in fluid communication with the pilot tube 272 via tubes 272a and 272b, respectively. By pushing fluid (such as air) through pilot tube 272, and thus 272a and 272b, the first expandable balloon 1000 and the second expandable balloon 1010 are inflated (as illustrated in FIG. 24). In the embodiment illustrated in FIG. 23 and FIG. 24, when the balloons 1000 and 1010 are inflated, the balloons 1000 and 1010 expand from an outer boundary of the aperture 170 towards the middle of the aperture 170 until they meet to substantially cover the aperture 170 to prevent medical gas from escaping. In an embodiment, the first expandable balloon 1000 and the second expandable balloon 1010 are low volume high pressure members. In an embodiment, the first expandable balloon 1000 and the second expandable balloon 1010 are high volume low pressure members. Although not illustrated in FIG. 23 and FIG. 24, in an embodiment, pilot tubes 272a and 272b each separately run longitudinally through the wall 110 of the tube so that each of the balloons 1000 and 1010 can independently be expanded or deflated.

Figure 25:
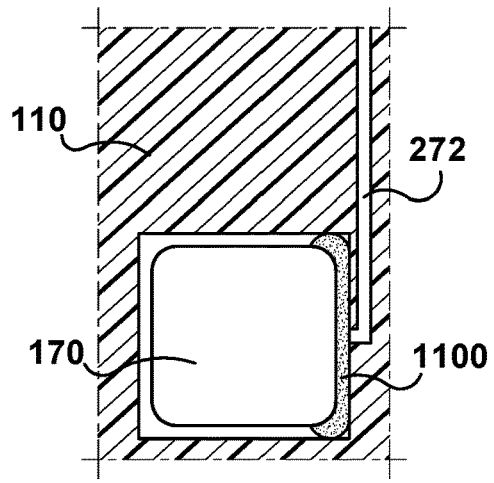
FIG. 25 and FIG. 26 show cutaway side views of the single lumen endobronchial tube of FIG. 1 showing an embodiment of a mechanism adapted to control the amount of medical gas passing through an aperture provided through a wall of the tube.
Figure 26:
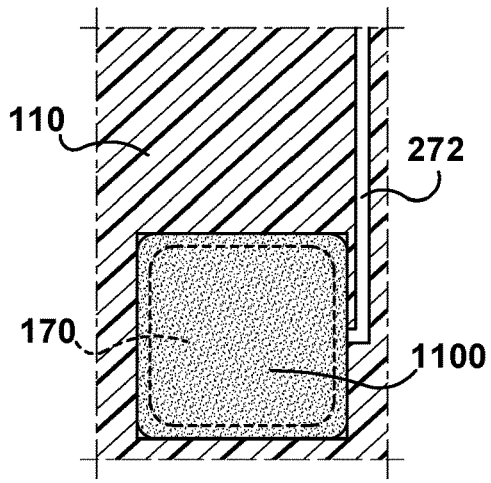

FIG. 25 in conjunction with FIG. 26 shows cutaway side views of a mechanism adapted to control the amount of medical gas passing through the aperture 170. The components of the mechanism are positioned within the wall 110 of the tube 100 such that the components are adapted to move in a frontal plane parallel to the central longitudinal axis of the tube 100 to cover the aperture 170 when required. As illustrated in FIG. 25, the mechanism includes an expandable balloon 1100 in fluid communication with the pilot tube 272. By pushing fluid (such as air) through pilot tube 272 the expandable balloon 1100 is inflated (as illustrated in FIG. 26). In the embodiment illustrated in FIG. 25 and FIG. 26, when the balloon 1100 is inflated, the balloon 1100 expands from a first outer boundary of the aperture 170 towards a second outer boundary of the aperture 170 to substantially cover the aperture 170 to prevent medical gas from escaping. In an embodiment, the expandable balloon 1100 is a low volume high pressure member. In an embodiment, the expandable balloon 1100 is a high volume low pressure member. Although the embodiments illustrated in FIG. 25 and FIG. 26 show the balloon 1100 positioned on the left outer boundary of the aperture 170, it should be understood that the balloon 1100 can be positioned on the right outer boundary of the aperture 170, the top outer boundary of the aperture 170 or on the bottom outer boundary of the aperture 170 and still be within the scope and spirit of the present disclosure.

Figure 27:
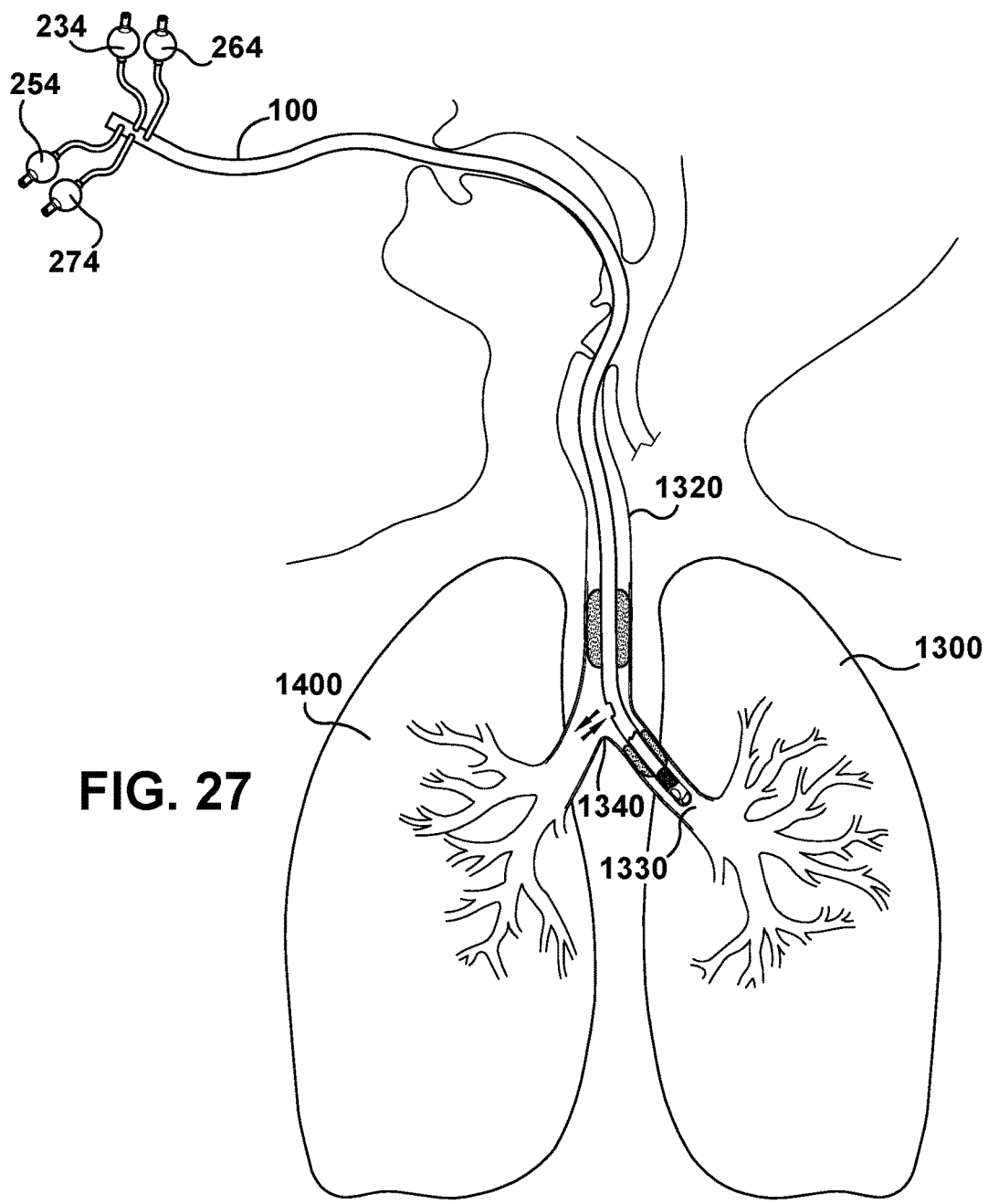
FIG. 27 shows a schematic view of the single lumen endobronchial tube of FIG. 1 positioned in a person for the selective ventilation of the right lung.

Referring to FIG. 27, the single lumen endobronchial tube 100 is positioned within a patient to facilitate artificial ventilation of the respiratory system. The single lumen endobronchial tube 100 has been placed within a mouth of the patient and positioned such that the tracheal portion 130 resides within the trachea 1320 and the bronchial portion 150 resides within the left main stem bronchi 1330. The tube 100 may be sufficiently designed such that the bronchial portion 150 curves for ease of placement beyond the carina 1340 into the left main stem bronchi 1330. In this placement, ventilation of the left lung or the right lung can be accomplished without having to move the single lumen endobronchial tube. Placement of the single lumen endobronchial tube 100 can be performed with or without fiberoptic visualization. Although FIG. 27 shows the single lumen endobronchial tube 100 being inserted through the mouth of the patient, it should be understood that the single lumen endobronchial tube 100 can also be inserted through the nasal passages into the airway passage. For one-lung ventilation of the right lung 1400, the aperture 170 remains open, which sufficiently allows the flow of medical gases through the aperture 170 and into the right lung. Once proper positioning of the single lumen endobronchial tube 100 in the pulmonary airway is determined, the bronchial cuff 152 is inflated to a desired pressure by pushing a fluid such as air or saline through the pilot tube 252 leading to the bronchial cuff 152. In an embodiment, the bronchial cuff 152 is inflated so that the bronchial cuff pressure (BCP) is in the range of about 15 cm $H_2O$ (about 11 mm Hg) to about 30 cm $H_2O$ (about 22 mm Hg). The tracheal cuff 132 is inflated by pushing a fluid such as air or saline through the pilot tube 232 leading to the tracheal cuff 132. In an embodiment, the tracheal cuff 132 is inflated so that the cuff pressure is in the range of about 15 cm $H_2O$ (about 11 mm Hg) to about 30 cm $H_2O$ (about 22 mm Hg). The seal formed by the tracheal cuff 132 is adapted to substantially provide a seal between the outside of the single lumen endobronchial tube 100 and the interior of the trachea 1320 in which the single lumen endobronchial tube 100 is inserted. The distal intraluminal balloon blocker 162 is inflated by pushing a fluid such as air or saline through the pilot tube 262 leading to the distal intraluminal balloon blocker 162. In an embodiment, the distal intraluminal balloon blocker 162 is inflated so that the cuff pressure is in the range of about 20 cm $H_2O$ (about 14.7 mm Hg) to about 95 cm $H_2O$ (about 69 mm Hg). The desired agent(s) are then introduced, for example from an anesthesia machine, through the lumen 160 of the tube 100 to deliver the desired agent(s) to the right lung 1400. The inflated distal intraluminal balloon blocker seals the lumen 160 of the tube 100 distal to the inflated distal intraluminal balloon blocker 162 such that sufficient blockage of the agents to the left lung 1300 is achieved.

Figure 28:
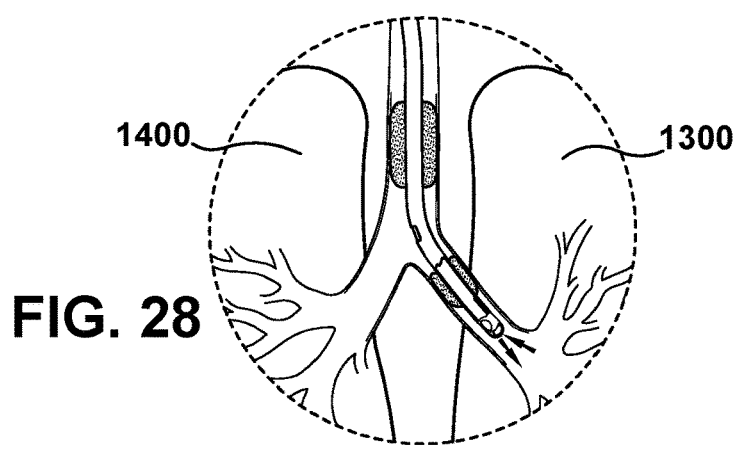
FIG. 28 shows a schematic view of the single lumen endobronchial tube of FIG. 1 positioned in a person for the selective ventilation of the left lung.

FIG. 28 shows the single lumen endobronchial tube 100 positioned during one-lung ventilation of the left lung 1300. The single lumen endobronchial tube 100 is placed in the pulmonary airway of a patient such that the tracheal portion 130 resides within the trachea 1320 and the bronchial portion 150 resides within the left main stem bronchi 1330. The tube 100 may be sufficiently designed such that the bronchial portion 150 curves for ease of placement beyond the carina 1340 into the left main stem bronchi 1330. Placement of the single lumen endobronchial tube 100 can be performed with or without fiberoptic visualization. For one-lung ventilation of the left lung, the aperture 170 is sealed to sufficiently preclude the flow of medical gases through the aperture 170 and into the right lung. Once proper positioning of the single lumen endobronchial tube 100 in the pulmonary airway is determined, the bronchial cuff 152 is inflated to a desired pressure by pushing a fluid such as air or saline through the pilot tube 252 leading to the bronchial cuff 152. In an embodiment, the bronchial cuff 152 is inflated so that the cuff pressure is in the range of about 15 cm $H_2O$ (about 11 mm Hg) to about 30 cm $H_2O$ (about 22 mm Hg). The seal formed by the bronchial cuff 152 is adapted to preclude any medical gas that has been forced into the patient's left lung from escaping through the left main stem bronchi 1330 into the trachea 1320. The tracheal cuff 132 is inflated by pushing a fluid such as air or saline through the pilot tube 232 leading to the tracheal cuff 132. In an embodiment, the tracheal cuff 132 is inflated so that the bronchial cuff pressure (BCP) is in the range of about 15 cm $H_2O$ (about 11 mm Hg) to about 30 cm $H_2O$ (about 22 mm Hg). The seal formed by the tracheal cuff 132 is adapted to substantially provide a seal between the outside of the single lumen endobronchial tube 100 and the interior of the trachea 1320 in which the single lumen endobronchial tube 100 is inserted. The desired agent(s) are then introduced, for example from an anesthesia machine, through the lumen 160 of the tube 100 to deliver the desired agent(s) to the left lung 1300.

It is also contemplated that in an alternative embodiment of the single lumen endobronchial tube, the distal intraluminal balloon blocker 162 (as well as the other co-dependent components of the distal intraluminal balloon blocker 162 including the pilot tube 262, the non-return valve 260 and the pilot balloon 264) are absent. In such an embodiment, a conventional endobronchial blocker can be used to block ventilation of the left main stem bronchi.

Figure 29:
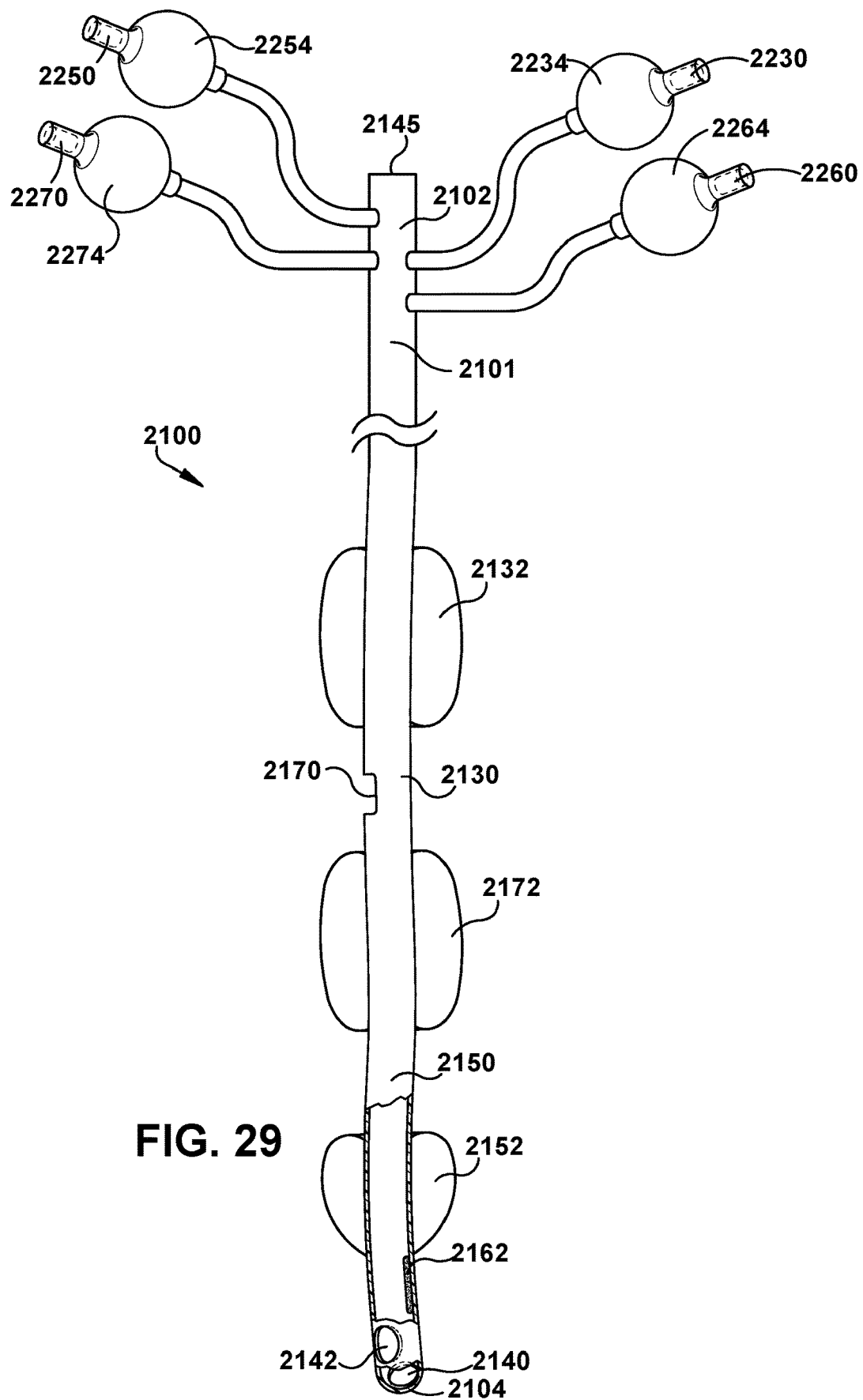
FIG. 29 is a side view of an embodiment of a single lumen endobronchial tube of the present disclosure.

FIG. 29 shows an embodiment of a single lumen endobronchial tube 2100 of the present disclosure. The single lumen endobronchial tube 2100 is a medical tube having a proximal end 2102, a distal end 2104, and a primary flow passage or lumen 2160 passing therebetween. The distal end 2104 of the tube 2100 has a bronchial opening 2140. In an embodiment, the bronchial opening 2140 is smooth and beveled, thus minimizing risk of tracheal intubation airway trauma. The distal end 2104 of the tube 2100 can optionally include a Murphy eye 2142, which is a distal opening in a wall 2110 and through an outer surface 2101 of the tube 2100 which can allow airflow in the event of the bronchial opening 2140 lying against the tracheal wall or being obstructed in other ways. Located at the proximal end 2102 of the tube 2100 is an opening 2145 sufficiently designed to connect with a mechanical ventilation device, including, but not limited to, an anesthesia machine or a PAP machine, with or without the use of an adaptor. The tube 2100 includes a tracheal portion 2130 and a bronchial portion 2150. The tube 2100 may be made from a flexible material including, but not limited to, latex, silicone, polyvinyl chloride (PVC), polyurethane (PU), polytetrafluoroethylene or a similar material that has met the American National Standard for Anesthetic Equipment; ANSI Z-79 standard and implant-tested to ensure nontoxicity. In an embodiment, the tube 2100 is made from a non-toxic, clear, PVC material. In an embodiment, the tracheal portion 2130 is adapted to follow the natural contour of a patient's trachea, and the bronchial portion 2150 is adapted to follow the natural contour of a patient's left main stem bronchi. In an embodiment, to facilitate passage of the bronchial portion 2150 into the left main stem bronchi, the tube 2100 is curved or bent and resembles the shape of a hockey stick. In an embodiment, the angle of the bend is about 45°. The lumen 2160 of the tube 2100 is sized and dimensioned to allow other instrumentation to pass through the lumen 2160 as required. The removal of mucous, the injection of medication, or the insertion of fiberoptic scopes for viewing within the tube 2100 are examples of the additional instrumentation capability which is afforded by the tube 2100. In an embodiment, the single lumen endobronchial tube 2100 may be referred to as a left-sided single lumen endobronchial tube.

A first tracheal cuff 2132, a second tracheal cuff 2172 and a bronchial cuff 2152 are spaced longitudinally along an exterior surface of the tracheal portion 2130 and the bronchial portion 2150, respectively. In an embodiment, the first tracheal cuff 2132, the second tracheal cuff 2172 and the bronchial cuff 2152 are thin walled, high volume low pressure (HVLP) balloon-like members sealed from fluid communication with the tube 2100 and adapted not to compromise the blood flow in the tracheal or bronchial wall when inflated. The first tracheal cuff 2132, the second tracheal cuff 2172, and the bronchial cuff 2152 are shown in an expanded state in FIG. 29. In an embodiment, the balloon-like members are spherical or elliptical in shape, although any desired shape is possible and within the scope and spirit of the present disclosure. In an embodiment, the walls of the first tracheal cuff 2132, the second tracheal cuff 2172 and the bronchial cuff 2152 are on the order of about 5 μm to about 500 μm, about 5 μm to about 250 μm, about 5 μm to about 100 μm, about 5 μm to about 50 μm, about 5 μm and about 20 μm, about 5 μm and about 15 μm. It is also contemplated that the walls may have a thickness of less than about 5 μm. Additionally, although the thickness of the walls may vary, it is desirable that the thickness of the material remain consistent throughout the cuff. A distal intraluminal balloon blocker 2162 adapted to inflate and deflate is positioned along an inner surface of the tube 2100 and when inflated acts to block flow by blocking ventilation to the left main stem bronchus. In an embodiment, the distal intraluminal balloon blocker 2162 is a low volume high pressure member. In an embodiment, the member is spherical or elliptical in shape, although any desired shape is possible and within the scope and spirit of the present disclosure.

The first tracheal cuff 2132, the second tracheal cuff 2172, the bronchial cuff 2152, and the distal intraluminal balloon blocker 2162 are each remotely and selectively inflatable through pilot tubes 2232, 2172, 2252 and 2262, respectively, running longitudinally through the wall of the tube 2100. The wall has an internal wall surface, an external wall surface and a thickness therebetween. Each pilot tube 2232, 2172, 2252 and 2262 emerges from the outer surface 2101 of the tube 2100 near the proximal end 2102 of the tube 2100. Attached to a proximal end of each pilot tube 2232, 2172, 2252 and 2262 is a non-return valve 2230, 2270, 2250 and 2260 which is adapted to receive the nozzle of a syringe (not visible) and a complementary indicator bladder 2234, 2274, 2254 and 2264 which enables an anesthesiologist to confirm that each of the first tracheal cuff 2132, the second tracheal cuff 2172, the bronchial cuff 2152, and the distal intraluminal balloon blocker 2162 has been inflated or deflated. The non-return valves 2230, 2270, 2250 and 2260 may be attached to a syringe for injecting a predetermined quantity of air. Various materials may be used to form the first tracheal cuff 2132, the second tracheal cuff 2172, the bronchial cuff 2152 and the distal intraluminal balloon blocker 2162. These materials include, but are not limited to, polyurethane (PU), low-density polyethylene (LDPE), polyvinyl chloride (PVC), silicone, neoprene, polyisoprene, polyamid (PA) or polyethylene teraphthalate (PETP). Additionally, copolymer admixtures for modifying the characteristics of the material may be used, for example a low density polyethylene and ethylene-vinylacetate copolymer (LDPE-EVA), or blends of the above mentioned materials (e.g. PU with PVC or PU with PA) would be considered suitable for forming the first tracheal cuff 2132, the second tracheal cuff 2172, the bronchial cuff 2152 and the distal intraluminal balloon blocker 2162.

An aperture 2170 is provided through the wall 2110 of the tube 2100 between the first tracheal cuff 2132 and the second tracheal cuff 2172. The aperture 2170 can be of any shape or size. In an embodiment, the aperture 2170 is dimensioned so that a fiberoptic scope can pass through the aperture 2170. In some embodiments, the single lumen endobrochial tube is adapted for use with a PAP machine. In such embodiments, conduits run longitudinally through the wall 2110 of the tube 2100 to deliver gas to a patient at positive pressure in order to hold open alveoli that would normally close at the end of expiration. The tube 2100 can be manufactured to various sizes and adapted to provide mechanical ventilation to an air-breathing animal in need thereof. In an embodiment, the tube 2100 is manufactured for human use and ranges in size from about 1.5 mm to about 11 mm in internal diameter (ID). In an embodiment, the tube 2100 is manufactured for human use and ranges in size from about 3 mm to about 10 mm in internal diameter (ID). In an embodiment, the tube 2100 is manufactured for non-human use and ranges in size from about 1.5 mm to about 40 mm in internal diameter (ID). In an embodiment, the tube 2100 is manufactured for non-human use and ranges in size from about 6 mm to about 40 mm in internal diameter (ID).

Figure 30:
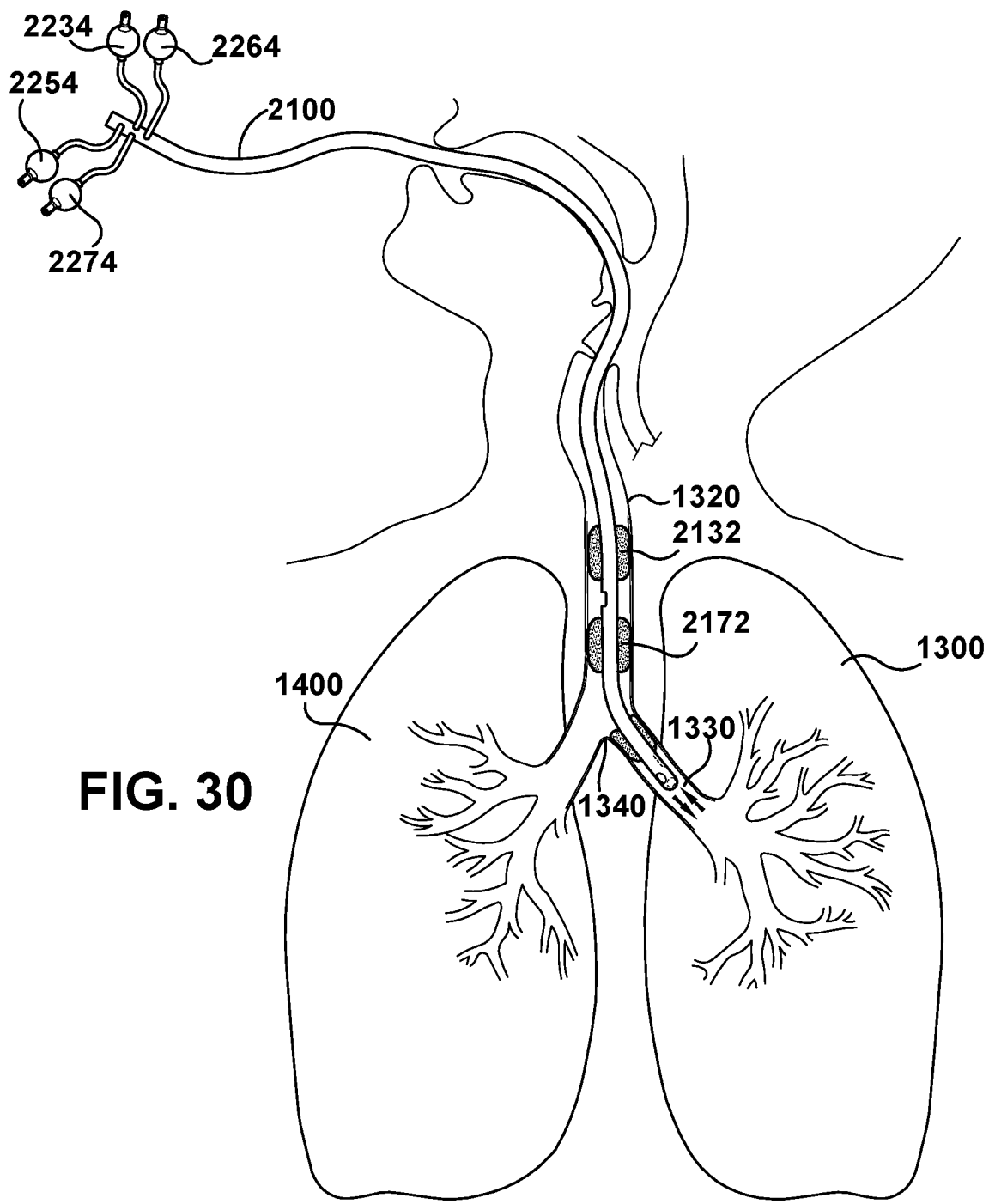
FIG. 30 shows a schematic view of the single lumen endobronchial tube of FIG. 29 positioned in a person for the selective ventilation of the left lung.

Referring to FIG. 30, the single lumen endobronchial tube 2100 is positioned within a patient to facilitate artificial ventilation of the respiratory system. The single lumen endobronchial tube 2100 has been placed within a mouth of the patient and positioned such that the tracheal portion 2130 resides within the trachea 1320 and the bronchial portion 2150 resides within the left main stem bronchi 1330. The tube 2100 may be sufficiently designed such that the bronchial portion 2150 curves for ease of placement beyond the carina 1340 into the left main stem bronchi 1330. In this placement, ventilation of the left lung or the right lung can be accomplished without having to move the lumen endobronchial tube. Placement of the lumen endobronchial tube can be performed with or without fiberoptic visualization. Although FIG. 30 shows the lumen endobronchial tube being inserted through the mouth of the patient, it should be understood that the lumen endobronchial tube can also be inserted through the nasal passages into the airway passage. Once proper positioning of the lumen endobronchial tube in the pulmonary airway is determined, the bronchial cuff 2152 is inflated to a desired pressure by pushing a fluid such as air or saline through the pilot tube 2252 leading to the bronchial cuff 2152. In an embodiment, the bronchial cuff 2152 is inflated so that the bronchial cuff pressure (BCP) is in the range of about 15 cm $H_2O$ (about 11 mm Hg) to about 30 cm $H_2O$ (about 22 mm Hg). The first tracheal cuff 2132 is inflated by pushing a fluid such as air or saline through the pilot tube 2232 leading to the first tracheal cuff 2132. The second tracheal cuff 2172 is inflated by pushing a fluid such as air or saline through the pilot tube 2272 leading to the second tracheal cuff 2172. In an embodiment, the first tracheal cuff 2132 and the second tracheal cuff 2172 are inflated so that the cuff pressure is in the range of about 15 cm $H_2O$ (about 11 mm Hg) to about 30 cm $H_2O$ (about 22 mm Hg). The seal formed by the tracheal cuffs 2132 and 2172 are adapted to substantially provide a seal between the outside of the lumen endobronchial tube and the interior of the trachea 1320 in which the tube 2100 is inserted. The desired agent(s) are then introduced, for example from an anesthesia machine, through the lumen 2160 of the tube 2100 to deliver the desired agent(s) to the left lung 1300. The closed space between the first tracheal cuff 2132 and the second tracheal cuff 2172 is adapted to block entry of the desired agent(s) to the right lung 1400. If the desired agent(s) are to be delivered into the right lung 1400 and not the left lung 1300, the procedure can proceed as follows: the second tracheal cuff 2172 is deflated, and the distal intraluminal balloon blocker 2162 is inflated by pushing a fluid such as air or saline through the pilot tube 2262 leading to the distal intraluminal balloon blocker 2162. In an embodiment, the distal intraluminal balloon blocker 2162 is inflated so that the cuff pressure is in the range of about 20 cm $H_2O$ (about 14.7 mm Hg) to about 95 cm $H_2O$ (about 69 mm Hg). The inflated distal intraluminal balloon blocker seals the lumen 2160 of the tube 2100 distal to the inflated distal intraluminal balloon blocker 2162 such that sufficient blockage of the agents to the left lung 1300 is achieved.

It is also contemplated that in an alternative embodiment of the single lumen endobronchial tube, the distal intraluminal balloon blocker 2162 (as well as the other co-dependent components of the distal intraluminal balloon blocker 2162 including the pilot tube 2262, the non-return valve 2260 and the pilot balloon 2264) are absent. In such an embodiment, a conventional endobronchial blocker can be used to block ventilation of the left main stem bronchi.

FIG. 31 shows an embodiment of a single lumen endobronchial tube 3100 of the present disclosure. The single lumen endobronchial tube 3100 is a medical tube having a proximal end 3102, a distal end 3104, and a primary flow passage or lumen 3160 passing therebetween. The distal end 3104 of the tube 3100 has a bronchial opening 3140. In an embodiment, the bronchial opening 3140 is smooth and beveled, thus minimizing risk of tracheal intubation airway trauma. The distal end 3104 of the tube 3100 can optionally include a Murphy eye 3142, which is a distal opening in a wall 3110 and through an outer surface 3101 of the tube 3100 which can allow airflow in the event of the bronchial opening 3140 lying against the tracheal wall or being obstructed in other ways. Located at the proximal end 3102 of the tube 3100 is an opening 3145 sufficiently designed to connect with a mechanical ventilation device, including, but not limited to, an anesthesia machine or a PAP machine, with or without the use of an adaptor. The tube 3100 includes a tracheal portion 3130 and a bronchial portion 3150. The tube 3100 may be made from a flexible material including, but not limited to, latex, silicone, polyvinyl chloride (PVC), polyurethane (PU), polytetrafluoroethylene or a similar material that has met the American National Standard for Anesthetic Equipment; ANSI Z-79 standard and implant-tested to ensure nontoxicity. In an embodiment, the tube 3100 is made from a non-toxic, clear, PVC material. In an embodiment, the tracheal portion 3130 is adapted to follow the natural contour of a patient's trachea, and the bronchial portion 3150 is adapted to follow the natural contour of a patient's left main stem bronchi. In an embodiment, to facilitate passage of the bronchial portion 150 into the left main stem bronchi, the tube 3100 is curved or bent and resembles the shape of a hockey stick. In an embodiment, the angle of the bend is about 45°. The lumen 3160 of the tube 3100 is sized and dimensioned to allow other instrumentation to pass through the lumen 3160 as required. The removal of mucous, the injection of medication, or the insertion of fiberoptic scopes for viewing within the tube 3100 are examples of the additional instrumentation capability which is afforded by the tube 3100. In an embodiment, the single lumen endobronchial tube 3100 may be referred to as a left-sided single lumen endobronchial tube.

A tracheal cuff 3132 and a bronchial cuff 3152 are spaced longitudinally along an exterior surface of the tracheal portion 3130 and the bronchial portion 3150, respectively. In an embodiment, the tracheal cuff 3132 and the bronchial cuff 3152 are thin walled, high volume low pressure (HVLP) balloon-like members sealed from fluid communication with the tube 3100 and adapted not to compromise the blood flow in the tracheal or bronchial wall when inflated. The tracheal cuff 3132 and the bronchial cuff 3152 are shown in an expanded state in FIG. 31. In an embodiment, the balloon-like members are spherical or elliptical in shape, although any desired shape is possible and within the scope and spirit of the present disclosure. In an embodiment, the walls of the tracheal cuff 3132 and the bronchial cuff 3152 are on the order of about 5 µm to about 500 µm, about 5 µm to about 250 µm, about 5 µm to about 100 µm, about 5 µm to about 50 µm, about 5 µm and about 20 µm, about 5 µm and about 15 µm. It is also contemplated that the walls may have a thickness of less than about 5 µm. Additionally, although the thickness of the walls may vary, it is desirable that the thickness of the material remain consistent throughout the cuff. A distal intraluminal balloon blocker 3162 adapted to inflate and deflate is positioned along an inner surface of the tube 3100 and when inflated acts to block flow by blocking ventilation to the left main stem bronchus. In an embodiment, the distal intraluminal balloon blocker 3162 is a low volume high pressure member. In an embodiment, the member is spherical or elliptical in shape, although any desired shape is possible and within the scope and spirit of the present disclosure.

The tracheal cuff 3132, the bronchial cuff 3152, and the distal intraluminal balloon blocker 3162 are each remotely and selectively inflatable through pilot tubes 3232, 3252 and 3262, respectively, running longitudinally through the wall 3110 of the tube 3100. The wall 3110 has an internal wall surface, an external wall surface and a thickness therebetween. Each pilot tube 3232, 3252 and 3262 emerges from the outer surface 3101 of the tube 3100 near the proximal end 3102 of the tube 3100. Attached to a proximal end of each pilot tube 3232, 3252 and 3262 is a non-return valve 3230, 3250 and 3260 which is adapted to receive the nozzle of a syringe (not visible) and a complementary indicator bladder 3234, 3254 and 3264 which enables an anesthesiologist to confirm that each of the tracheal cuff 3132, the bronchial cuff 3152, and the distal intraluminal balloon blocker 3162 has been inflated or deflated. The non-return valves 3230, 3250 and 3260 may be attached to a syringe for injecting a predetermined quantity of air. Various materials may be used to form the tracheal cuff 3132, the bronchial cuff 3152 and the distal intraluminal balloon blocker 3162. These materials include, but are not limited to, polyurethane (PU), low-density polyethylene (LDPE), polyvinyl chloride (PVC), silicone, neoprene, polyisoprene, polyamid (PA) or polyethylene teraphthalate (PETP). Additionally, copolymer admixtures for modifying the characteristics of the material may be used, for example a low density polyethylene and ethylene-vinylacetate copolymer (LDPE-EVA), or blends of the above mentioned materials (e.g. PU with PVC or PU with PA) would be considered suitable for forming the tracheal cuff 3132, the bronchial cuff 3152 and the distal intraluminal balloon blocker 3162. It is also contemplated that in an alternative embodiment of the single lumen endobronchial tube, the distal intraluminal balloon blocker 3162 (as well as the other co-dependent components of the distal intraluminal balloon blocker 3162 including the pilot tube 3262, the non-return valve 3260 and the pilot balloon 3264) are absent. In such an embodiment, a conventional endobronchial blocker can be used to block ventilation of the left main stem bronchi.

Figure 34:
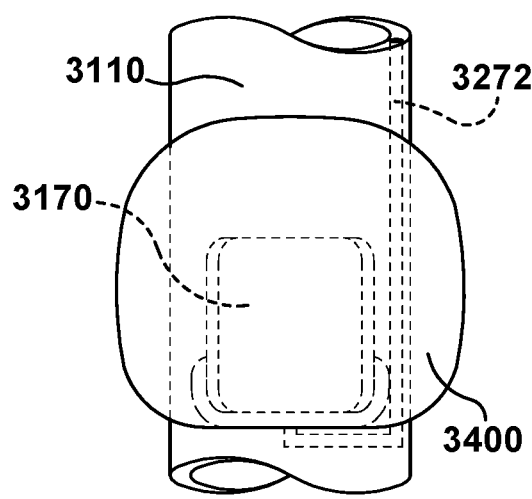

An aperture 3170 is provided through the wall 3110 of the tube 3100 between the tracheal cuff 3132 and the bronchial cuff 3152. The aperture 3170 can be of any shape or size. In an embodiment, the aperture 3170 is dimensioned so that a fiberoptic scope can pass through the aperture 3170. An expandable balloon 3400 is sufficiently designed to seal the aperture 3170. The expandable balloon 3400 is adapted to control the amount of medical gas passing through the aperture 3170. In an embodiment, the expandable balloon 3400 is adapted to completely close and seal the aperture 3170 such that the amount of medical gas passing through the aperture 3170 from the lumen 3160 is 0%. The expandable balloon 3400 is shown in an expanded state in FIG. 31. As illustrated in FIG. 32, which is a cross-sectional plan view taken along line 32-32 of FIG. 31, when the expandable balloon 3400 is inflated, the expandable balloon 3400 is sufficiently designed to seal up against a trachea and the pressure inside the expandable balloon 3400 keeps the aperture 3170 closed. The expandable balloon 3400 closes the aperture 3170 yet does not herniate into the lumen 3160 of the tube 3100. If the expandable balloon 3400 inflates from the distal border of the aperture 3170 (as illustrated in FIG. 34) conceivably any air leakage from the aperture 3170 would get trapped in a tracheal space formed by the tracheal cuff 3132 and the expandable balloon 3400. In an embodiment, the expandable balloon 3400 is a thin walled, high volume low pressure (HVLP) member sealed from fluid communication with the tube 3100 and adapted not to compromise the blood flow in the tracheal or bronchial wall when inflated. In an embodiment, the expandable balloon 3400 is spherical or elliptical in shape, although any desired shape is possible and within the scope and spirit of the present disclosure. In an embodiment, the walls of the expandable balloon 3400 are on the order of about 5 µm to about 500 µm, about 5 µm to about 250 µm, about 5 µm to about 100 µm, about 5 µm to about 50 µm, about 5 µm and about 20 µm, about 5 µm and about 15 µm. It is also contemplated that the walls may have a thickness of less than about 5 µm. Additionally, although the thickness of the walls may vary, it is desirable that the thickness of the material remain consistent throughout the cuff. In an embodiment, the expandable balloon 3400 is remotely controlled through a pilot tube 3272 running longitudinally through the wall 3110 of the tube (see FIG. 32). The pilot tube 3272 emerges from the outer surface 3101 near the proximal end 3102 of the tube 3100. Attached to a proximal end of the pilot tube 3272 is a non-return valve 3270 which is adapted to receive the nozzle of a syringe (not visible), and an indicator bladder 3274 which enables an anesthesiologist to confirm that the expandable balloon 3400 has been inflated to close or seal the aperture 3170. The non-return valve 3270 may be attached to a syringe for injecting a predetermined quantity of air, saline or any other fluid.

In some embodiments, the single lumen endobrochial tube is adapted for use with a PAP machine. In such embodiments, conduits run longitudinally through the wall 3110 of the tube 3100 to deliver gas to a patient at positive pressure in order to hold open alveoli that would normally close at the end of expiration. The tube 3100 can be manufactured to various sizes and adapted to provide mechanical ventilation to an air-breathing animal in need thereof. In an embodiment, the tube 3100 is manufactured for human use and ranges in size from about 1.5 mm to about 11 mm in internal diameter (ID). In an embodiment, the tube 3100 is manufactured for human use and ranges in size from about 3 mm to about 10 mm in internal diameter (ID). In an embodiment, the tube 3100 is manufactured for non-human use and ranges in size from about 1.5 mm to about 40 mm in internal diameter (ID). In an embodiment, the tube 3100 is manufactured for non-human use and ranges in size from about 6 mm to about 40 mm in internal diameter (ID).

Figure 33:
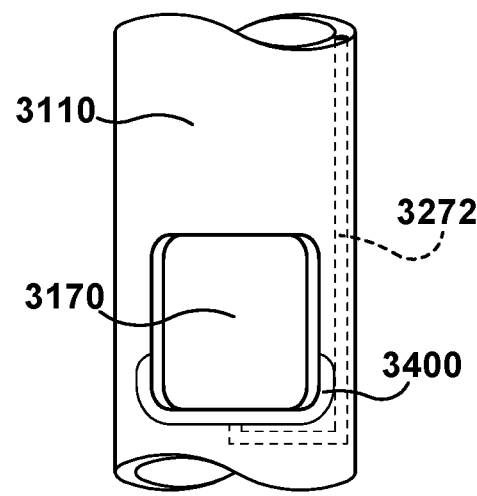
FIG. 33 and FIG. 34 show cutaway side views of the single lumen endobronchial tube of FIG. 31 showing an embodiment of a balloon adapted to control the amount of medical gas passing through an aperture provided through a wall of the tube.

FIG. 33 in conjunction with FIG. 34 shows cutaway side views of the expandable balloon 3400 adapted to control the amount of medical gas passing through the aperture 3170. As illustrated in FIG. 33, the expandable balloon 3400 is in fluid communication with the pilot tube 3272. By pushing fluid (such as air) through pilot tube 3272 the expandable balloon 3400 is inflated (as illustrated in FIG. 34). When the expandable balloon 3400 is inflated, the expandable balloon 3400 seals up against the trachea and the pressure keeps the aperture 3170 closed. The expandable balloon 3400 closes the aperture 3170 yet does not herniate into the lumen 3160 of the tube 3100. If the expandable balloon 3400 inflates from the distal border of the aperture 3170 (as illustrated in FIG. 34) conceivably any air leakage from the aperture 3170 would get trapped in a tracheal space formed by the tracheal cuff 3132 and the expandable balloon 3400. Although the embodiments illustrated in FIG. 33 and FIG. 34 show the expandable balloon 3400 positioned on the bottom outer boundary of the aperture 3170, it should be understood that the balloon 3400 can be positioned on the right outer boundary of the aperture 3170, the top outer boundary of the aperture 3170 or on the left outer boundary of the aperture 3170 and still be within the scope and spirit of the present disclosure.

Figure 35:
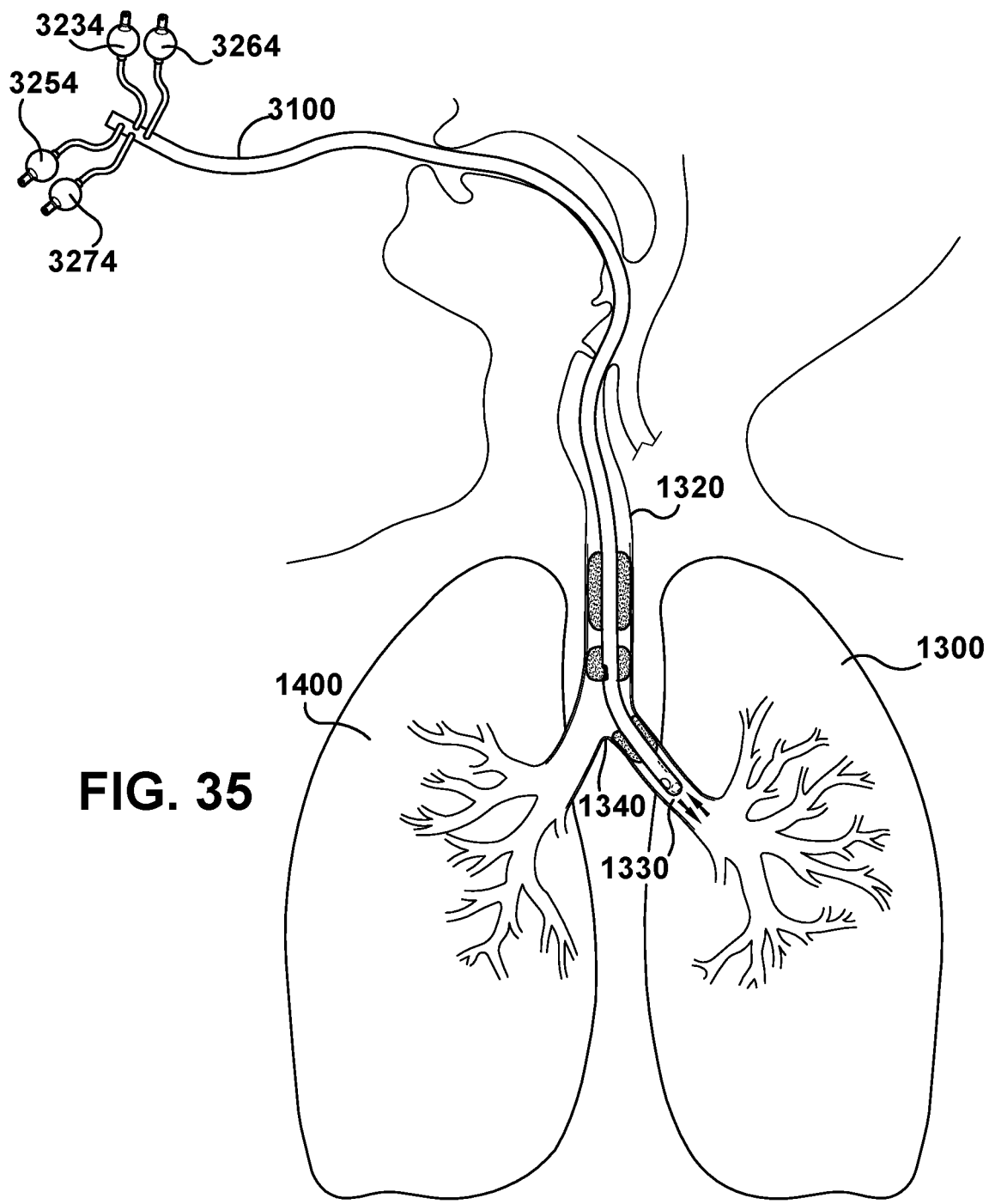
FIG. 35 shows a schematic view of the single lumen endobronchial tube of FIG. 31 positioned in a person for the selective ventilation of the left lung.

Referring to FIG. 35, the single lumen endobronchial tube 3100 is positioned within a patient to facilitate artificial ventilation of the respiratory system. The single lumen endobronchial tube 3100 has been placed within a mouth of the patient and positioned such that the tracheal portion 3130 resides within the trachea 1320 and the bronchial portion 3150 resides within the left main stem bronchi 1330. The tube 3100 may be sufficiently designed such that the bronchial portion 3150 curves for ease of placement beyond the carina 1340 into the left main stem bronchi 1330. In this placement, ventilation of the left lung or the right lung can be accomplished without having to move the tube 3100. Placement of the single lumen endobronchial tube 3100 can be performed with or without fiberoptic visualization. Although FIG. 35 shows the single lumen endobronchial tube 3100 being inserted through the mouth of the patient, it should be understood that the single lumen endobronchial tube 3100 can also be inserted through the nasal passages into the airway passage. Once proper positioning of the single lumen endobronchial tube 3100 in the pulmonary airway is determined, the bronchial cuff 3152 is inflated to a desired pressure by pushing a fluid such as air or saline through the pilot tube 3252 leading to the bronchial cuff 3152. In an embodiment, the bronchial cuff 3152 is inflated so that the bronchial cuff pressure (BCP) is in the range of about 15 cm $H_2O$ (about 11 mm Hg) to about 30 cm $H_2O$ (about 22 mm Hg). The tracheal cuff 3132 is inflated by pushing a fluid such as air or saline through the pilot tube 3232 leading to the tracheal cuff 3132. In an embodiment, the tracheal cuff 3132 is inflated so that the cuff pressure is in the range of about 15 cm $H_2O$ (about 11 mm Hg) to about 30 cm $H_2O$ (about 22 mm Hg). The seal formed by the tracheal cuff 3132 is adapted to substantially provide a seal between the outside of the tube 3100 and the interior of the trachea 1320 in which the tube 3100 is inserted. The expandable balloon 3400 is inflated by pushing a fluid such as air or saline through the pilot tube 3272 leading to the expandable balloon 3400. When the expandable balloon 3400 is inflated, the expandable balloon 3400 seals up against the trachea 1320 and the pressure keeps the aperture 3170 closed. In an embodiment, the expandable balloon 3400 closes the aperture 3170 without herniating into the lumen 3160 of the tube 3100. When the expandable balloon 3400 inflates from the distal border of the aperture 3170 (as illustrated in FIG. 34) any air that may leak from the aperture 3170 would get trapped in a tracheal space formed by the tracheal cuff 3132 and the expandable balloon 3400. The desired agent(s) are then introduced, for example from an anesthesia machine, through the lumen 3160 of the tube 3100 to deliver the desired agent(s) to the left lung 1300. The closed space between the tracheal cuff 3132 and the expandable balloon 3400 is adapted to block entry of the desired agent(s) to the right lung 1400. If the desired agent(s) are to be delivered into the right lung 1400 and not the left lung 1300, the procedure can proceed as follows: the expandable balloon 3400 is deflated, and the distal intraluminal balloon blocker 3162 is inflated by pushing a fluid such as air or saline through the pilot tube 3262 leading to the distal intraluminal balloon blocker 3162. In an embodiment, the distal intraluminal balloon blocker 3162 is inflated so that the cuff pressure is in the range of about 20 cm $H_2O$ (about 14.7 mm Hg) to about 95 cm $H_2O$ (about 69 mm Hg). The inflated distal intraluminal balloon blocker seals the lumen 3160 of the tube 3100 distal to the inflated distal intraluminal balloon blocker 3162 such that sufficient blockage of the agents to the left lung 1300 is achieved.

Endobronchial tube displacement may result in lifethreatening complications and continuous direct vision of the position of the endobronchial tube may enable safer management. In an embodiment, any of the single lumen endobronchial tubes disclosed herein may further include a built-in video camera having an optional built-in light source. The video camera is connected to a monitor via a cable that runs longitudinally through the wall of the tube. The video camera and cable are embedded within the common tube wall. In an embodiment, the view from the video camera appears continuously on the monitor in the anaesthetist's vicinity. In an embodiment, the video camera terminates at a location that is distal to the aperture that is provided through the wall of the tube between the tracheal balloon cuff and the bronchial balloon cuff. The placement of the video camera at this location may provide for a better view of the carina of the trachea, the cartilaginous ridge within the trachea that runs anteroposteriorly between the two primary bronchi at the site of the tracheal bifurcation at the lower end of the trachea. This may help ensure that the bronchial portion of the single lumen endobronchial tube is positioned below the carina. In embodiments where the single lumen endobronchial tube includes a built-in video camera, it may not be necessary to use a fiberoptic scope during placement, use, or removal of the tube.

FIG. 36 in conjunction with FIG. 37 shows an embodiment of a single lumen endobronchial tube 4100 of the present disclosure. The single lumen endobronchial tube 4100 is a medical tube that includes a built-in video camera 4300 having an optional built-in light source. The video camera 4300 is connected to a monitor 4350 via a cable 4332 that runs longitudinally through the wall 4110 of the tube 4100. The video camera 4300 and cable 4332 are embedded within the common tube wall 4110. In an embodiment, the view from the video camera 4300 appears continuously on the monitor 4350 in the anaesthetist's vicinity. The single lumen endobronchial tube 4100 has a proximal end 4102, a distal end 4104, and a primary flow passage or lumen 4160 passing therebetween. The distal end 4104 of the tube 4100 has a bronchial opening 4140. In an embodiment, the bronchial opening 4140 is smooth and beveled, thus minimizing risk of tracheal intubation airway trauma. The distal end 4104 of the tube 4100 can optionally include a Murphy eye 4142, which is a distal opening in a wall 4110 and through an outer surface 4101 of the tube 4100 which can allow airflow in the event of the bronchial opening 4140 lying against the tracheal wall or being obstructed in other ways. Located at the proximal end 4102 of the tube 4100 is an opening 4145 sufficiently designed to connect with a mechanical ventilation device, including, but not limited to, an anesthesia machine or a PAP machine, with or without the use of an adaptor. The tube 4100 includes a tracheal portion 4130 and a bronchial portion 4150. The tube 4100 may be made from a flexible material including, but not limited to, latex, silicone, polyvinyl chloride (PVC), polyurethane (PU), polytetrafluoroethylene or a similar material that has met the American National Standard for Anesthetic Equipment; ANSI Z-79 standard and implant-tested to ensure nontoxicity. In an embodiment, the tube 4100 is made from a non-toxic, clear, PVC material. In an embodiment, the tracheal portion 4130 is adapted to follow the natural contour of a patient's trachea, and the bronchial portion 4150 is adapted to follow the natural contour of a patient's left main stem bronchi. In an embodiment, to facilitate passage of the bronchial portion 4150 into the left main stem bronchi, the tube 4100 is curved or bent and resembles the shape of a hockey stick. In an embodiment, the angle of the bend is about 45°. The lumen 4160 of the tube 4100 is sized and dimensioned to allow other instrumentation to pass through the lumen 4160 as required. The removal of mucous, the injection of medication, or the insertion of fiberoptic scopes for viewing within the tube 4100 are examples of the additional instrumentation capability which is afforded by the tube 4100. In an embodiment, the single lumen endobronchial tube 4100 may be referred to as a left-sided single lumen endobronchial tube.

A tracheal cuff 4132 and a bronchial cuff 4152 are spaced longitudinally along an exterior surface of the tracheal portion 4130 and the bronchial portion 4150, respectively. In an embodiment, the tracheal cuff 4132 and the bronchial cuff 4152 are thin walled, high volume low pressure (HVLP) balloon-like members sealed from fluid communication with the tube 4100 and adapted not to compromise the blood flow in the tracheal or bronchial wall when inflated. The tracheal cuff 4132 and the bronchial cuff 4152 are shown in an expanded state in FIG. 36. In an embodiment, the balloonlike members are spherical or elliptical in shape, although any desired shape is possible and within the scope and spirit of the present disclosure. In an embodiment, the walls of the tracheal cuff 4132 and the bronchial cuff 4152 are on the order of about 5 μm to about 500 μm, about 5 μm to about 250 μm, about 5 μm to about 100 μm, about 5 μm to about 50 μm, about 5 μm and about 20 μm, about 5 μm and about 15 μm. It is also contemplated that the walls may have a thickness of less than about 5 μm. Additionally, although the thickness of the walls may vary, it is desirable that the thickness of the material remain consistent throughout the cuff. A distal intraluminal balloon blocker 4162 adapted to inflate and deflate is positioned along an inner surface of the tube 4100 and when inflated acts to block flow by blocking ventilation to the left main stem bronchus. In an embodiment, the distal intraluminal balloon blocker 4162 is a low volume high pressure member. In an embodiment, the member is spherical or elliptical in shape, although any desired shape is possible and within the scope and spirit of the present disclosure.

The tracheal cuff 4132, the bronchial cuff 4152, and the distal intraluminal balloon blocker 4162 are each remotely and selectively inflatable through pilot tubes 4232, 4252 and 2624, respectively, running longitudinally through the wall 4110 of the tube 4100 as shown in FIG. 37. The wall 4110 has an internal wall surface, an external wall surface and a thickness therebetween. Each pilot tube 4232, 4252 and 4262 emerges from the outer surface 4101 of the tube 4100 near the proximal end 4102 of the tube 4100. The cable 4332 also emerges from the outer surface 4101 of the tube 4100 near the proximal end 4102 of the tube 4100. Attached to a proximal end of each pilot tube 4232, 4252 and 4262 is a non-return valve 4230, 4250 and 4260 which is adapted to receive the nozzle of a syringe (not visible) and a complementary indicator bladder 4234, 4254 and 4264 which enables an anesthesiologist to confirm that each of the tracheal cuff 4132, the bronchial cuff 4152, and the distal intraluminal balloon blocker 4162 has been inflated or deflated. The non-return valves 4230, 4250 and 4260 may be attached to a syringe for injecting a predetermined quantity of air. Various materials may be used to form the tracheal cuff 4132, the bronchial cuff 4152 and the distal intraluminal balloon blocker 4162. These materials include, but are not limited to, polyurethane (PU), low-density polyethylene (LDPE), polyvinyl chloride (PVC), silicone, neoprene, polyisoprene, polyamid (PA) or polyethylene teraphthalate (PETP). Additionally, copolymer admixtures for modifying the characteristics of the material may be used, for example a low density polyethylene and ethylene-vinylacetate copolymer (LDPE-EVA), or blends of the above mentioned materials (e.g. PU with PVC or PU with PA) would be considered suitable for forming the tracheal cuff 4132, the bronchial cuff 4152 and the distal intraluminal balloon blocker 4162. It is also contemplated that in an alternative embodiment of the single lumen endobronchial tube, the distal intraluminal balloon blocker 4162 (as well as the other co-dependent components of the distal intraluminal balloon blocker 4162 including the pilot tube 4262, the non-return valve 4260 and the pilot balloon 4264) are absent. In such an embodiment, a conventional endobronchial blocker can be used to block ventilation of the left main stem bronchi.

An aperture 4170 is provided through the wall 4110 of the tube 4100 between the tracheal cuff 4132 and the bronchial cuff 4152, as best illustrated in FIG. 36. The aperture 4170 can be of any shape or size. In an embodiment, the aperture 4170 is dimensioned so that a fiberoptic scope can pass through the aperture 170. The amount of medical gas passing through the aperture 4170 can be controlled using any of the mechanisms described above with reference to FIGS. 4-26. In an embodiment, the components of the mechanism are adapted to completely close and seal the aperture 4170 such that the amount of medical gas passing through the aperture 4170 from the lumen 4160 is 0%. In an embodiment, the components of the mechanism are adapted to partially close the aperture 4170 such that the amount of medical gas passing through the aperture 4170 from the lumen 4160 is greater than 0% but less than 100%.

In some embodiments, the single lumen endobronchial tube 4100 is adapted for use with a PAP machine. In such embodiments, conduits 4282 and 4292 (see FIG. 36) run longitudinally through the wall 4110 of the tube 4100 to deliver gas to a patient at positive pressure in order to hold open alveoli that would normally close at the end of expiration. The tube 4100 can be manufactured to various sizes and adapted to provide mechanical ventilation to an air-breathing animal in need thereof. In an embodiment, the tube 4100 is manufactured for human use and ranges in size from about 1.5 mm to about 11 mm in internal diameter (ID). In an embodiment, the tube 4100 is manufactured for human use and ranges in size from about 3 mm to about 10 mm in internal diameter (ID). In an embodiment, the tube 4100 is manufactured for non-human use and ranges in size from about 1.5 mm to about 40 mm in internal diameter (ID). In an embodiment, the tube 4100 is manufactured for non-human use and ranges in size from about 6 mm to about 40 mm in internal diameter (ID).

Figure 38:
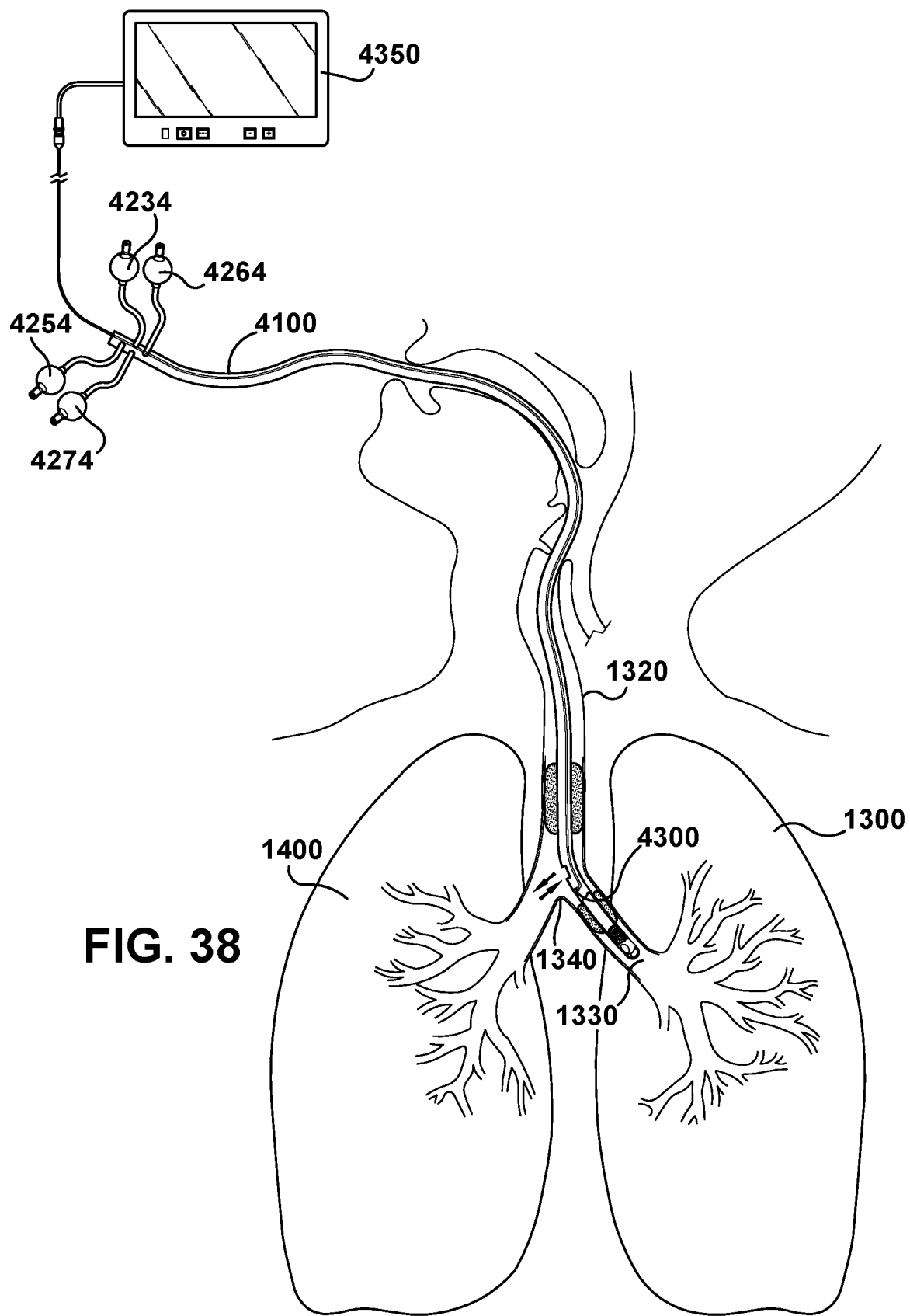
FIG. 38 shows a schematic view of the single lumen endobronchial tube of FIG. 36 positioned in a person for the selective ventilation of the right lung.

Referring to FIG. 38, the single lumen endobronchial tube 4100 is positioned within a patient to facilitate artificial ventilation of the respiratory system. The single lumen endobronchial tube 4100 has been placed within a mouth of the patient and positioned such that the tracheal portion 4130 resides within the trachea 1320 and the bronchial portion 4150 resides within the left main stem bronchi 1330. The tube 4100 may be sufficiently designed such that the bronchial portion 4150 curves for ease of placement beyond the carina 1340 into the left main stem bronchi 1330. In this placement, ventilation of the left lung or the right lung can be accomplished without having to move the tube 4100. Placement of the single lumen endobronchial tube 4100 can be performed with the aid of the video camera 4300 and monitor 4350. Although FIG. 38 shows the single lumen endobronchial tube 4100 being inserted through the mouth of the patient, it should be understood that the single lumen endobronchial tube 4100 can also be inserted through the nasal passages into the airway passage. For one-lung ventilation of the right lung 1400, the aperture 4170 remains open, which sufficiently allows the flow of medical gases through the aperture 4170 and into the right lung. Once proper positioning of the single lumen endobronchial tube 4100 in the pulmonary airway is determined, the bronchial cuff 4152 is inflated to a desired pressure by pushing a fluid such as air or saline through the pilot tube 4252 leading to the bronchial cuff 4152. In an embodiment, the bronchial cuff 4152 is inflated so that the bronchial cuff pressure (BCP) is in the range of about 15 cm $H_2O$ (about 11 mm Hg) to about 30 cm $H_2O$ (about 22 mm Hg). The tracheal cuff 4132 is inflated by pushing a fluid such as air or saline through the pilot tube 4232 leading to the tracheal cuff 4132. In an embodiment, the tracheal cuff 4132 is inflated so that the cuff pressure is in the range of about 15 cm $H_2O$ (about 11 mm Hg) to about 30 cm $H_2O$ (about 22 mm Hg). The seal formed by the inflated tracheal cuff 4132 is adapted to substantially provide a seal between the outside of the tube 4100 and the interior of the trachea 1320 in which the single lumen endobronchial tube 4100 is inserted. The distal intraluminal balloon blocker 4162 is inflated by pushing a fluid such as air or saline through the pilot tube 4262 leading to the distal intraluminal balloon blocker 4162. In an embodiment, the distal intraluminal balloon blocker 4162 is inflated so that the cuff pressure is in the range of about 20 cm $H_2O$ (about 14.7 mm Hg) to about 95 cm $H_2O$ (about 69 mm Hg). The desired agent(s) are then introduced, for example from an anesthesia machine, through the lumen 4160 of the tube 4100 to deliver the desired agent(s) to the right lung 1400. The inflated distal intraluminal balloon blocker seals the lumen 4160 of the tube 4100 distal to the inflated distal intraluminal balloon blocker 4162 such that sufficient blockage of the agents to the left lung 1300 is achieved.

For one-lung ventilation of the left lung 1300, the single lumen endobronchial tube 4100 is placed in the pulmonary airway of a patient such that the tracheal portion 4130 resides within the trachea 1320 and the bronchial portion 4150 resides within the left main stem bronchi 1330. The tube 4100 may be sufficiently designed such that the bronchial portion 4150 curves for ease of placement beyond the carina 1340 into the left main stem bronchi 1330. Placement of the single lumen endobronchial tube 4100 can be performed with the aid of the video camera 4300 and monitor 4350. For one-lung ventilation of the left lung, the aperture 4170 is sealed to sufficiently preclude the flow of medical gases through the aperture 4170 and into the right lung. Once proper positioning of the single lumen endobronchial tube 4100 in the pulmonary airway is determined, the bronchial cuff 4152 is inflated to a desired pressure by pushing a fluid such as air or saline through the pilot tube 4252 leading to the bronchial cuff 4152. In an embodiment, the bronchial cuff 4152 is inflated so that the cuff pressure is in the range of about 15 cm $H_2O$ (about 11 mm Hg) to about 30 cm $H_2O$ (about 22 mm Hg). The seal formed by the bronchial cuff 4152 is adapted to preclude any medical gas that has been forced into the patient's left lung from escaping through the left main stem bronchi 1330 into the trachea 1320. The tracheal cuff 4132 is inflated by pushing a fluid such as air or saline through the pilot tube 4232 leading to the tracheal cuff 4132. In an embodiment, the tracheal cuff 4132 is inflated so that the bronchial cuff pressure (BCP) is in the range of about 15 cm $H_2O$ (about 11 mm Hg) to about 30 cm $H_2O$ (about 22 mm Hg). The seal formed by the tracheal cuff 4132 is adapted to substantially provide a seal between the outside of the tube 4100 and the interior of the trachea 1320 in which the single lumen endobronchial tube 4100 is inserted. The desired agent(s) are then introduced, for example from an anesthesia machine, through the lumen 4160 of the tube 4100 to deliver the desired agent(s) to the left lung 1300.

In an embodiment, a single lumen endobronchial tube of the present disclosure can be used in general anesthesia, intensive care, and emergency medicine for airway management and mechanical ventilation. In an embodiment, a single lumen endobronchial tube of the present disclosure can be used during any procedure where lung separation is necessary to isolate and selectively ventilate a single lung, including, but not limited to, thoracic surgical procedures, lung abscess surgical procedures, and pulmonary hemorrhage surgical procedures. In some embodiments, a single lumen endobronchial tube of the present disclosure is used with a BiPAP machine. In some embodiments, a single lumen endobronchial tube of the present disclosure is used with a CPAP machine. In such embodiments, the proximal end of the medical tube is connected to the PAP machine such that compressed air is delivered directly to the pulmonary airway of a patient. Use of a single lumen endobronchial tube of the present disclosure in conjunction with a CPAP machine may be useful in treating or preventing various conditions in patients, including, but not limited to, obstructive sleep apnea and respiratory failure.

In some embodiments, a single lumen endobronchial tube of the present disclosure is used with an anesthesia machine. In such embodiments, the proximal end of the medical tube is connected to the anesthesia machine such that medical gases are delivered to the pulmonary airway of an air-breathing animal. Use of a single lumen endobronchial tube of the present disclosure in conjunction with an anesthesia machine may be useful to support the administration of anesthesia to the animal.

A method of selective left lung bronchial occlusion for right lung ventilation of a patient includes inserting a single lumen endobronchial tube into the pulmonary airway of a patient, the tube having: a lumen extending throughout the tube's entire length with an opening at each of opposed distal and proximal ends of the tube, the opening at the proximal end of the tube being adapted for connection to an external mechanical ventilation device, and the opening at the distal end of the tube being adapted for delivery of a medical gas; a wall extending throughout the tube's entire length having an internal wall surface, an external wall surface and a thickness therebetween, a portion of the wall having an aperture and a shaft adapted to house a mechanism for sealing the aperture; a distal bronchial cuff positioned along the external wall surface and adapted to expand radially outward; a proximal tracheal cuff positioned along the external wall surface and adapted to expand radially outward; and a distal intraluminal balloon blocker at a respective distal location relative to the aperture; positioning the tube in the pulmonary airway such that the distal bronchial cuff is in the left main stem bronchus, and the proximal tracheal cuff is in the trachea; inflating the distal bronchial cuff radially outwardly to seal against the surrounding bronchus of the left lung; inflating the proximal tracheal cuff radially outwardly to seal against the surrounding trachea of the patient; inflating the distal intraluminal balloon blocker radially outwardly to occlude the lumen of the tube and thereby effectively occlude the left lung, whereby an airway from the ventilation device to the patient's right lung is maintained via the aperture.

A method of selective right lung bronchial occlusion for left lung ventilation of a patient includes inserting a single lumen endobronchial tube into the pulmonary airway of a patient, the tube having: a lumen extending throughout the tube's entire length with an opening at each of opposed distal and proximal ends of the tube, the opening at the proximal end of the tube being adapted for connection to an external mechanical ventilation device, and the opening at the distal end of the tube being adapted for delivery of a medical gas; a wall extending throughout the tube's entire length having an internal wall surface, an external wall surface and a thickness therebetween, a portion of the wall having an aperture and a shaft adapted to house a mechanism for sealing the aperture; a distal bronchial cuff positioned along the external wall surface and adapted to expand radially outward; a proximal tracheal cuff positioned along the external wall surface and adapted to expand radially outward; and a distal intraluminal balloon blocker at a respective distal location relative to the aperture; positioning the tube in the pulmonary airway such that the distal bronchial cuff is in the left main stem bronchus, and the proximal tracheal cuff is in the trachea; inflating the distal bronchial cuff radially outwardly to seal against the surrounding bronchus of the left lung; inflating the proximal tracheal cuff radially outwardly to seal against the surrounding trachea of the patient; and sealing the aperture by activating the mechanism housed in the shaft of the wall of the tube to block the aperture and thereby effectively occlude the right lung, whereby an airway from the ventilation device to the patient's left lung is maintained via the opening at the distal end of the tube.

A method for one-lung ventilation of a lung of an air-breathing animal includes providing a single lumen endobronchial tube, the single lumen endobronchial tube comprising a medical tube having a single lumen with an opening at each of opposed distal and proximal ends of the tube, the opening at the proximal end of the tube being adapted for connection to an external mechanical ventilation device, and the opening at the distal end of the tube being adapted for delivery of a medical gas; a wall extending throughout the tube's entire length having an internal wall surface, an external wall surface and a thickness therebetween, a portion of the wall having an aperture and a shaft adapted to house a mechanism for sealing the aperture; a distal bronchial cuff positioned along the external wall surface and adapted to expand radially outward; at least a first proximal tracheal cuff positioned along the external wall surface and adapted to expand radially outward; and a distal intraluminal balloon blocker at a respective distal location relative to the aperture; positioning the single lumen endobronchial tube in the pulmonary airway of the animal such that the distal bronchial cuff is in the left main stem bronchus, and the first proximal tracheal cuff is in the trachea, wherein a distal end of the medical tube is positioned beyond the carina of the animal; connecting the proximal end of the medical tube to the external mechanical ventilation device; inflating the distal bronchial cuff radially outwardly to seal against the surrounding bronchus of the left lung; inflating the proximal tracheal cuff radially outwardly to seal against the surrounding trachea of the animal; and performing a step selected from one of inflating the distal intraluminal balloon blocker radially outwardly to occlude the lumen of the tube and thereby effectively occlude the left lung, whereby an airway from the ventilation device to the animal's right lung is maintained via the aperture or sealing the aperture by activating the mechanism housed in the shaft of the wall of the tube to block the aperture and thereby effectively occlude the right lung, whereby an airway from the ventilation device to the anima's left lung is maintained via the opening at the distal end of the tube.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for one-lung ventilation of a lung of an air-breathing animal comprising:
   providing a single lumen endobronchial tube, the single lumen endobronchial tube comprising:
      a medical tube having a single lumen with an opening at each of opposed distal and proximal ends of the tube, the opening at the proximal end of the tube being adapted for connection to an external mechanical ventilation device, and the opening at the distal end of the tube being adapted for delivery of a medical gas;
      a wall extending throughout a length of the tube and having an internal wall surface, an external wall surface and a thickness therebetween, a portion of the wall having an aperture sealed by a mechanism similar in size to the aperture;
      a distal bronchial inflatable cuff positioned along the external wall surface and adapted to expand radially outward;
      at least a first proximal tracheal inflatable cuff positioned along the external wall surface and adapted to expand radially outward; and
      a distal intraluminal balloon blocker at a respective distal location relative to the aperture;
   positioning the single lumen endobronchial tube in the pulmonary airway of the animal such that the distal bronchial inflatable cuff is in the left main stem bronchus, and the first proximal tracheal inflatable cuff is in the trachea, wherein a distal end of the medical tube is positioned beyond the carina of the animal;
   connecting the proximal end of the medical tube to the external mechanical ventilation device;
   inflating the distal bronchial inflatable cuff radially outwardly to seal against the surrounding bronchus of the left lung;
   inflating the proximal tracheal inflatable cuff radially outwardly to seal against the surrounding trachea of the animal; and performing a step selected from one of:
   delivering the medical gas through the medical tube to ventilate the left lung, or
   delivering the medical gas through the medical tube to ventilate the right lung by inflating the distal intraluminal balloon blocker radially outwardly to occlude the lumen of the tube to effectively occlude the left lung and unsealing the aperture.

2. The method of claim 1 wherein the air-breathing animal is a human and the medical tube has an internal diameter ranging from about 1.5 mm to about 11.0 mm.

3. The method of claim 1 wherein the air-breathing animal is a non-human and the medical tube has an internal diameter ranging from about 1.5 mm to about 40.0 mm.

4. The method of claim 1 wherein the single lumen endobronchial tube further comprises a built-in video camera embedded within the tube wall for real-time visualization.

5. The method of claim 1 wherein the distal intraluminal balloon blocker is a low volume high pressure member.

6. The method of claim 1 wherein the first proximal tracheal inflatable cuff, the distal bronchial inflatable cuff and the distal intraluminal balloon blocker are each remotely and selectively inflatable.

7. The method of claim 1 wherein the tube wall of the endobronchial tube further comprises at least one conduit for the passage of a gas.

* * * * *